(12) United States Patent
Akaike

(10) Patent No.: US 11,866,752 B2
(45) Date of Patent: Jan. 9, 2024

(54) CYSTEINE POLYSULFIDATION AND MITOCHONDRIAL BIOENERGETICS REGULATED BY CYSTEINYL-TRNA SYNTHETASE

(71) Applicants: Bio-Xcelerator, Inc., Tokyo (JP); TOHOKU UNIVERSITY, Sendai (JP)

(72) Inventor: Takaaki Akaike, Sendai (JP)

(73) Assignees: Bio-Xcelerator, Inc., Tokyo (JP); TOHOKU UNIVERSITY, Sendai (JP)

( * ) Notice: Subject to any disclaimer, the term of this patent is extended or adjusted under 35 U.S.C. 154(b) by 0 days.

(21) Appl. No.: 17/471,638

(22) Filed: Sep. 10, 2021

(65) Prior Publication Data

US 2021/0403963 A1    Dec. 30, 2021

Related U.S. Application Data

(63) Continuation of application No. 17/188,982, filed on Mar. 1, 2021, now abandoned, which is a continuation of application No. 16/655,553, filed on Oct. 17, 2019, now abandoned.

(60) Provisional application No. 62/911,632, filed on Oct. 7, 2019, provisional application No. 62/747,229, filed on Oct. 18, 2018.

(51) Int. Cl.
  *C12P 13/12*   (2006.01)
  *C12P 13/02*   (2006.01)

(52) U.S. Cl.
  CPC ....... *C12P 13/02* (2013.01); *C12Y 601/01016* (2013.01)

(58) Field of Classification Search
  CPC .................................................... C12P 13/12
  See application file for complete search history.

(56) References Cited

U.S. PATENT DOCUMENTS 5,206,439 A    4/1993   Shaw

FOREIGN PATENT DOCUMENTS

JP    S57-112367 A    7/1982
JP    H5-255235 A    10/1993

OTHER PUBLICATIONS

Akaike T et al. Cysteinyl-tRNA synthetase governs cysteine polysulfidation and mitochondrial bioenergetics. 2017. Nature Communications. p. 1-15 (Year: 2017).*
W. Chen et al, Rational Design of a Dual-Reactivity-Based Fluorescent Probe for Visualizing Intracellular HSNO, Angewandte Chemie, Sep. 3, 2019, p. 16067-16070.
Nishimura et al, Mitochondrial cysteinyl-tRNA synthetase is expressed via alternative transcriptional initiation regulated by energy metabolism in yeast cells, Journal of Biological Chemistry (JBC), vol. 294, Issue 37, p. 13781-13788, Sep. 13, 2019.
M. Feelisch, Long-lasting blood pressure lowering effects of nitrite are NO-independent and mediated by hydrogen peroxide, persulfides, and oxidation of protein kinase G1α redox signalling, Cardiovascular Research, Jan. 1, 2020, pp. 51-62, vol. 116, Issue 1.
A. Nishimura et al, Depolysulfidation of Drp1 induced by low-dose methylmercury exposure increases cardiac vulnerability to hemodynamic overload, Science Signaling, vol. 12, Issue 587, Jun. 25, 2019.
C. Yang et al, Data-Driven Identification of Hydrogen Sulfide Scavengers, Angewandte Chemie, 131, p. 11014-11018, Jun. 13, 2019.
Rudyk et al, Oxidation of PKGIα mediates an endogenous adaptation to pulmonary hypertension, PNAS, 116 (26), p. 13016-13025, Jun. 2019.
M. Akiyama et al, Environmental Electrophile-Mediated Toxicity in Mice Lacking Nrf2, CSE, or Both, Environmental Health Perspectives, vol. 127 (6) Jun. 2019.
Y. Kyogoku et al, Nitrosative stress in patients with asthma-chronic obstructive pulmonary disease overlap, Journal of Allergy and Clinical Immunology, 2019.
M. Ikeda et al, Distribution of Polysulfide in Human Biological Fluids and Their Association with Amylase and Sperm Activities, Molecules, vol. 24, 1689, 2019.
T. Zhang et al, Enhanced Cellular Polysulfides Negatively Regulate TLR4 Signaling and Mitigate Lethal Endotoxin Shock, Cell Chemical Biology, 26, 686-698, May 16, 2019.
T. Takata, The active-site cysteine residue of Ca2+/calmodulin-dependent protein kinase I is protected from irreversible modification via generation of polysulfidation, Nitric Oxide, 86, p. 68-75, 2019.
Y. Kishimoto et al, 8-Nitro-cGMP attenuates context-dependent fear memory in mice, Biochemical and Biophysical Research Communications (BBRC), 511, p. 141-147, 2019.
J. Lin et al, The Uptake and Release of Polysulfur Cysteine Species by Cells: Physiological and Toxicological Implications, Chemical Research in Toxicology, 32, p. 447-455, 2019.
S. Fujii et al, Persulfide synthases that are functionally coupled with translation mediate sulfur respiration in mammalian cells, British Journal of Pharmacology, 176, p. 607-615, 2019.
C. Bianco et al, The reaction of hydrogen sulfide with disulfides: formation of a stable trisulfide and implications for biological systems, British Journal of Pharmacology, 176, p. 671-683, 2019.
H. Hamid et al, Polysulfide stabilization by tyrosine and hydroxyphenyl-containing derivatives that is important for a reactive sulfur metabolomics analysis, Redox Biology, 21, 101096, 2019.
V. Bogdandi, Speciation of reactive sulfur species and their reactions with alkylating agents: do we have any clue about what is present inside the cell?, British Journal of Pharmacology, 176, p. 646-670, 2019.
S Khan et al., Reactive Persulfides from Salmonella Typhimurium Downregulate Autophagy-Mediated Innate Immunity in Macrophages by Inhibiting Electrophilic Signaling, Cell Chemical Biology, 25, p. 1403-1413, Nov. 15, 2018.
A. Nishimura et al, Hypoxia-induced interaction of filamin with Drp1 causes mitochondrial hyperfission-associated myocardial senescence, Science Signaling, 11, Nov. 13, 2018.

(Continued)

*Primary Examiner* — Paul J Holland
(74) *Attorney, Agent, or Firm* — Muncy, Geissler, Olds & Lowe, P.C.

(57) ABSTRACT

A method of synthesize cysteine hydropersulfide (CysSSH) includes taking a substrate L-cysteine, and performing a reaction catalyzed by cysteinyl-tRNA synthetases (CARSs).

4 Claims, 13 Drawing Sheets

Specification includes a Sequence Listing.

(56) References Cited

OTHER PUBLICATIONS

J. Fukuto et al, Biological hydropersulfides and related polysulfides—a new concept and perspective in redox biology; FFBS Letters, 5892, p. 2140-2152, 2018.
D. Heppner et al, Cysteine perthiosulfenic acid (Cys-SSOH): A novel intermediate in thiolbased redox signaling?, Redox Biology, 14, p. 349-385, 2018.
Office Action of the corresponding JP application No. 2019-239945 dated Oct. 31, 2023 and English translation thereof.

* cited by examiner

SEQUENCE LISTING

```
<160> NUMBER OF SEQ ID NOS: 16

<210> SEQ ID NO 1
<211> LENGTH: 1386
<212> TYPE: DNA
<213> ORGANISM: Escherichia coli

<400> SEQUENCE: 1
atgctaaaaa tcttcaatac tctgacacgc caaaagagg aatttaagcc tattcacgcc      60
ggggaagtcg gcatgtacgt gtgtggaatc accgtttacg atctctgtca tatcggtcac     120
gggcgtacct tgttgctttt tgacgtggtt gcgcgctatc tgcgtttcct cggctataaa     180
ctgaagtatg tgcgcaacat taccgatatc gacgacaaaa tcatcaaacg cgccaatgaa     240
aatggcgaaa gctttgtggc gatggtggat cgcatgatcg ccgaaatgca caaagatttt     300
gatgctttga acattctgcg cccggatatg gagccgcgcg cgacgcacca tatcgcagaa     360
attattgaac tcactgaaca actgatcgcc aaaggtcacg cttatgtggc ggacaacggc     420
gacgtgatgt tcgacgtccc gaccgatcca acttatggcg tgctgtcgcg tcaggatctc     480
gaccagctgc aggcaggcgc gcgcgttgac gtggtcgacg acaaacgcaa cccaatggac     540
ttcgttctgt ggaagatgtc gaaagagggc gaaccgagct ggccgtctcc gtggggcgcg     600
ggtcgtcctg gctggcacat tgaatgttcg gcaatgaact gcaagcagct gggtaaccac     660
tttgatatcc acggcggcgg ttcagacctg atgttcccgc accacgaaaa cgaaatcgcg     720
cagtccacct gtgcccatga tggtcagtat gtgaactact ggatgcactc ggggatggtg     780
atggttgacc gcgagaagat gtccaaatcg ctgggtaact tctttaccgt gcgcgatgtg     840
ctgaaatact acgacgcgga aaccgtgcgt tacttcctga tgtcgggcca ctatcgcagc     900
cagttgaact acagcgaaga gaacctgaag caggcgcgtg cggcgctgga gcgtctctac     960
actgcgctgc gcgcacaga taaaaccgtt gcgcctgccg gtggcgaagc gtttgaagcg    1020
cgctttattg aagcgatgga cgacgatttc aacacccgg aagcctattc cgtactgttt    1080
gatatggcgc gtgaagtaaa ccgtctgaaa gcagaagata tggcagcggc gaatgcaatg    1140
gcatctcacc tgcgtaaact ttccgctgta ttgggcctgc tggagcaaga accggaagcg    1200
ttcctgcaaa gcggcgcgca ggcagacgac agcgaagtgg ctgagattga agcgttaatt    1260
caacagcgtc tggatgcccg taaagcgaaa gactgggcgg cggcggatgc ggcgcgtgat    1320
cgtcttaacg agatggggat cgtgctggaa gatggcccgc aagggaccac ctggcgtcgt    1380
aagtaa                                                             1386

<210> SEQ ID NO 2
<211> LENGTH: 1695
<212> TYPE: DNA
<213> ORGANISM: Homo sapiens

<400> SEQUENCE: 2
```

```
atgttgagga ctacgcgcgg cccaggcctg ggcccccgc tgctccaggc cgcgctgggc    60
cttgggcggg ctgggtggca ctggcctgcg ggccgggcgg cgagcggggg gcgcgggcgg   120
gcctggctgc agcccacggg ccgggagacg ggtgtgcagg tgtacaacag cctcaccggg   180
aggaaggaac ccctaatcgt ggcgcacgcc gaagccgcct cctggtatag ctgtggacca   240
actgtatatg atcatgcgca ccttggccat gcttgctcat atgttagatt tgatatcatt   300
cgaaggatcc taaccaaggt ttttggatgc agcatagtca tggtgatggg tattacagat   360
gtagatgata aaatcatcaa agagccaatg agatgaata tttcccccgc ttccctcgcc   420
agtctttatg aggaagactt caagcaggac atggcagccc tgaaggttct cccacccacg   480
gtgtacctga gggtaaccga aaatattcct cagataattt ctttcattga aggaatcatt   540
gctcgtggga acgcttattc aacggcaaaa ggcaatgtct acttcgatct gaagtctaga   600
ggagacaagt atggcaaatt ggtcggcgtg gtccctggtc cagtcggaga gccagcggac   660
tctgacaagc gtcatgccag tgacttcgcc ctgtggaagg cggccaaacc ccaggaggtg   720
ttctgggcct ctccctgggg acccggggag ccggctggc acatcgagtg ctctgccatc   780
gctagtatgg tatttggaag tcaactggat atccattcag gtgggataga tttagctttt   840
ccacatcatg aaaacgaaat tgcacagtgc gaagtctttc atcagtgcga gcagtgggga   900
aattattttc tgcattctgg gcatttgcac gccaaaggca agaagaaaa aatgtccaaa   960 tcattaaaga actacattac tattaaggac tttctgaaga ccttttcccc cgatgtcttc  1020
cggttcttct gcctgcggag cagctaccgc tcagccatcg actacagtga cagcgccatg  1080
ctccaagctc agcagctgct cctggggctg ggctctttcc tggaggacgc acgtgcctac  1140
atgaaggggc agctggcctg cggctccgtc agggaagcga tgctgtggga gaggctctcc  1200
agcaccaaga gggccgtgaa ggcggccttg gcagatgatt ttgacacacc cagggtggtt  1260
gatgccatcc tgggccttgc acaccacggg aatggacagc tcagggcgtc cctgaaggaa  1320
cctgaagggc cgagaagtcc tgctgtgttt ggtgccatca tctcttactt tgaacagttt  1380
tttgaaactg ttggaatttc tctggcaaat caacagtacg tttcaggaga cggcagcgag  1440
gctaccttgc atggtgtggt ggacgagctg gtgcggttcc ggcagaaggt ccggcagttt  1500
gcgctggcca tgcccgaggc cacggggggac gcccggcggc agcagctcct agaaaggcag  1560
cccctgctgg aagcatgcga caccctgcgc cggggcctga ctgcccacgg catcaacatc  1620
aaggacagaa gcagtacaac atccacgtgg gaactgctgg atcaaaggac aaaagaccaa  1680
aaatcagcgg gctga                                                  1695

<210> SEQ ID NO 3
<211> LENGTH: 1659
<212> TYPE: DNA
<213> ORGANISM: Mus musculus

<400> SEQUENCE: 3
atgctgcggg cgcgcgggcc tgggcccggc gctctgctgc tccgggccgc gctgggtctc    60
gggcggcgcg gcggtcatg gcaacggccg caaggccagg acaccggcgt gcaggtgcat   120
aacagcctca ctggcaggaa ggagccgctg atagtggccc gctcggacgc agtctcctgg   180
tatagctgtg gaccgactgt gtacgaccat gcacatcttg gccatgcttg ctcctatgtt   240
agatttgaca ttatccggag gatcctgacc agagtgtttg gatgcaatgt ggtcatggcg   300
atgagcatta ccgacgtgga tgacaaaata atcaagagag ctaacgagat gaacgtgacg   360
cccgcttctc tcgccagtct ttttgaggaa gaatttaaac aagacatggc agccctgaag   420
```

```
gttctgccgc caactgtgta tttgagagtc actgagaaca tccctcagat cattgctttc    480
atcgagggca tcattgctca cggccatgca tactcgacag ctacaggcag cgtctacttc    540
gatctgcacg cccgagggga caagtatggc aagctggtca cacggttcc cagtgccact    600 gcagagccag caggtgactc tgacaagcgg cacagcagcg acttcgccct gtggaaggca    660
gccaaacctc aggaggtgtt ctgggcttcg ccgtggggag acggacggcc tggatggcac    720
atcgagtgct ctaccatggc cagtgaggtg ttcggaagcc acctggacat ccacaccggc    780
ggcatagact ggctttccc acatcacgaa aatgaaatcg cgcagagtga agtcttccac    840
cagtgtcagc agtggggaaa ttacttccta cattctggtc atttgcatgt gaaaggcaca    900
gaagaaaaga tgtccaaatc cctaaaaaac tatatcacca ttaaggactt cctgaagacc    960
ttctcccctg acgtcttccg ctttttctgc ttgcgtacca actataggtc agccattgaa   1020
tacagtgaca gtaccttggt ggaagccaag cacctcctgc tggggctggc ctcttttgtg   1080
gaggatgcac gagcctacgt aaaggggcag ctgacctgtg ccctgttga ggaggatgtg    1140 ctatgggaga ggctgactag caccaagaag gcggtgaaag ctgctctagc caatgacttt   1200
gacacaccga gggcagtgaa caccatcctg gaccttgtgc accatgcaaa cagacagctc   1260
agggcggtct ccaaggaagc tagtggccca aggagtccca ctgtgtttgg ggccatcatt   1320
tcctacgttg agcagttttt cgagactgtt gggatttctc tggcaaatcg acagtgtgtt   1380
tcaggagaca gcagcacagt aacgttgcgc tgtgtggtag atgaactcgt gcgcttcagg   1440
ctgaaggtcc gccagtatgc actggacaca cccggggctg ctggggaggc tcggaaacgg   1500
cagctccagg aaaggcagcc cttgctggag gcatgtgaca cactccgaca ggacctcgtc   1560
acccatggca tcaatgttaa ggacagaggc agtgcagcct ccacatggga actgctggat   1620
ccaaggacaa gacaccagaa acctggggac cgaggatga                          1659

<210> SEQ ID NO 4
<211> LENGTH: 273
<212> TYPE: DNA
<213> ORGANISM: Artificial Sequence
<220> FEATURE:
<223> OTHER INFORMATION: synthesised

<400> SEQUENCE: 4
ggttcgcccg gctgggcctg gcctgcagga tcttgccttc cgcctgttcg ctggatctgt     60
ccccaatatg ctgcgggcgc gcgggcctgg gcccggcgct ctgctgctcc gggccgcgct    120
gggtctcggg cggcgcgggc ggtcatggca acggccgcaa ggccaggaca ccggcgtgca    180
ggtgcataac agcctcactg gcaggaagga gccgctgata gtggcccgct cggacgcagt    240
ctcctggtgc gtgcgccggg agaggcaggg cgg                                 273

<210> SEQ ID NO 5
<211> LENGTH: 74
<212> TYPE: DNA
<213> ORGANISM: Artificial Sequence
<220> FEATURE:
<223> OTHER INFORMATION: synthesised

<400> SEQUENCE: 5
ggttcgcccg gctgggcctg gcctgcagga tcttgccttc cgccttggtg cgtgcgccgg     60
gagaggcagg gcgg                                                       74

<210> SEQ ID NO 6
```

```
<211> LENGTH: 2247
<212> TYPE: DNA
<213> ORGANISM: Mus musculus

<400> SEQUENCE: 6
atggcaggtt cctccgcgga gcagggtaaa ggccggcgag tgcagcctca gtggtccccc      60
ccagcaggga ctgagccctg caggctccgc tctataata gcctcacccg gaacaaggat     120
gtatttatac ctcaagatgg gaagaaggtg acgtggtact gttgcgggcc gactgtctat     180
gatgcgtctc acatgggaca tgccaggtcc tacatctcct tcgatatcct gaggagggtg     240
ctgagggatt acttccagta tgatgtcttt tactgcatga acatcacaga cattgatgat     300
aagatcatca ggcgggcacg gcagaactac ctgtttgagc agtatcggga gcagaaaccc     360
ccagccaccc agctcctgaa ggatgtccgt gatgccatga agccattttc agtcaagtta     420
agtgagacaa cagatcccga caagaggcag atgctggagc ggatccagaa ctctgtgaaa     480
cttgccacag aaccactgga acaggctgtg cgatccagcc tctctggaga ggaagtagac     540
agcaaagtac aggtgttgct ggaggaagca aaggacttgc tctctgactg gctggattcc     600
acaggtggca gtgaggtgac tgacaactcg atttttctcca aactgcccaa gttctgggaa     660 gaaagagttcc acaaagacat ggaagccctg aatgttctcc ctcctgatgt cctaacccgt     720
gtcagtgaat atgtgccaga aattgtgaac ttcgtccaga agattgtgga caatggttat     780
ggttatgctt caaatggatc tgtttacttc gacacagcca gtttgctgc tagtgaaaag     840 cactcctatg gaagctggt gcctgaggcc gttggggatc agaaggcact tcaggaaggg     900
gaaggtgatc tgagcatctc tgctgaccgc ttagtgaga aacgctctcc caatgacttt     960
gccttgtgga aggcctccaa gccaggcgag ccatcctggc cttgcccctg gggaaagggt    1020
cgtcccggat ggcacataga gtgttctgct atggcaggca cgctcctggg agcctcaatg    1080
gacattcatg gtggagggtt tgacctccgc ttcccccacc atgacaatga gctggcacag    1140
tcggaggcct actttgaaaa tgactgctgg gtcaggtact tcttgcacac gggccacttg    1200
acgatagcag gctgcaagat gtccaagtca ctgaaaaact ttatcaccat taaagatgcc    1260
ttgaagaagc actcagcacg gcagctgcga ctggcattcc tcatgcactc atggaaagac    1320
acactggact attccagcaa cactatggag tctgctcttc agtatgaaaa attcatgaac    1380
gagtttttct aaatgtgaa agacatcctc cgagcccctg tagacatcac tggccagttt    1440
gaaaagtggg aagctgaaga agtggagcta aataagaact tctatggcaa gaagaccgca    1500
gttcacgaag ccttgtgtga taacattgac acccggactg tcatggaaga gatgcgggct    1560
ttggtcagtc agtgcaacct ctacatggca gccaggaagg ctgaacggag gaggcccaac    1620
cgggctctgc tggagaacat tgccatgtac ctcacccaca tgctgaagat ctttggggcc    1680
atagaggagg agagccccct ggggttccca gttggtgggc ctggaaccaa cctgaacctc    1740
gagtcaacag tcatgcccta ccttcaggtg ttatcagaat tcagagaggg agtacgaaag    1800
attgcccgag agaaaaaagt tcttgaggtt ctacagctca gtgatgccct ccgggatgac    1860
atcctgcctg agcttggggt ccggtttgaa gaccatgaag gctgccaac agtggtgaag    1920 ttggtggaca gagacacctt actgaaagag aaggaaggaa agaaaagggc tgaagaagag    1980
aagaggagga gaaagaggga ggcggccaga aagaaacagg agcaagaagc agcaaagctg    2040
gccaagatga agataccacc cagtgagatg ttcctgtcag aagtcaacaa gtattctaaa    2100
tttgatgaaa atggtctgcc tacccacgac accgaaggca aagagctgag caagggccag    2160
gccaagaagc tgaagaagct ctttgaagcc caggagaaac tgtacaagga gtatctgcaa    2220
```

```
atgttacaga atggcagcct ccagtga                                        2247
```

<210> SEQ ID NO 7
<211> LENGTH: 2496
<212> TYPE: DNA
<213> ORGANISM: Homo sapiens

<400> SEQUENCE: 7

```
atggcagatt cctccgggca gcaggctcct gactacaggt ccattctgag cattagtgac     60
gaggcagcca gggcacaagc cctgaacgag cacctcagca cgcgtagcta tgtccagggg    120
tactcactgt cccaggcaga cgtggacgcg ttcaggcagc tctcggcccc gcccgctgac    180
ccccagctct tccacgtggc tcggtggttc aggcacatag aagcgctcct gggtagcccc    240
tgtggcaaag ccagccctg caggctccaa gcaagcaaag gccggcgtgt gcagccccag    300
tggtcccctc ctgctgggac ccagccatgc agactccacc tttacaacag cctcaccagg    360
aacaaggaag tgttcatacc tcaagatggg aaaaaggtga cgtggtattg ctgtgggcca    420
accgtctatg acgcatctca catggggcac gccaggtcct acatctcttt tgatatcttg    480
agaagagtgt tgaaggatta cttcaaattt gatgtctttt attgcatgaa cattacggat    540
attgatgaca agatcatcaa gagggcccgg cagaaccacc tgttcgagca gtatcgggag    600
aagaggcctg aagcggcaca gctcttggag gatgttcagg ccgccctgaa gccattttca    660
gtaaaattaa atgagaccac ggatcccgat aaaaagcaga tgctcgaacg gattcagcac    720
gcagtgcagc ttgccacaga gccacttgag aaagctgtgc agtccagact cacgggagag    780
gaagtcaaca gctgtgtgga ggtgttgctg aagaagcca aggatttgct ctctgactgg    840
ctggattcta cacttggctg tgatgtcact gacaattcca tcttctccaa gctgcccaag    900
ttctgggagg gggacttcca cagagacatg gaagctctga atgttctccc tccagatgtc    960
ttaacccggg ttagtgagta tgtgccagaa attgtgaact tgtccagaa gattgtggac   1020
aacggttacg gctatgtctc caatgggtct gtctactttg atacagcgaa gtttgcttct   1080
agcgagaagc actcctatgg gaagctggtg cctgaggccg ttggagatca gaaagccctt   1140
caagaagggg aaggtgacct gagcatctct gcagaccgcc tgagtgagaa gcgctctccc   1200
aacgactttg ccttatggaa ggcctctaag cccggagaac cgtcctggcc gtgcccttgg   1260
ggaaagggtc gtccgggctg gcatatcgag tgctcggcca tggcaggcac cctcctaggg   1320
gcttcgatgg acattcacgg aggtgggttc gacctccggt tcccccacca tgacaatgag   1380
ctggcacagt cggaggccta ctttgaaaac gactgctggg tcaggtactt cctgcacaca   1440
ggccacctga ccattgcagg ctgcaaaatg tcaaagtcac taaaaaactt catcaccatt   1500
aaagatgcct tgaaaagca ctcagcacgg cagttgcggc tggccttcct catgcactcg   1560
tggaaggaca ccctggacta ctccagcaac accatggagt cagcgcttca atatgagaag   1620
ttcttgaatg agttttttctt aaatgtgaaa gatatccttc gcgctcctgt tgacatcact   1680
ggtcagtttg agaagtgggg agaagaagaa gcagaactga ataagaactt ttatgacaag   1740
aagacagcaa ttcacaaagc cctctgtgac aatgttgaca cccgcaccgt catggaagag   1800
atgcgggcct tggtcagtca gtgcaacctc tatatgcag cccggaaagc cgtgaggaag   1860
aggcccaacc aggctctgct ggagaacatc gccctgtacc tcacccatat gctgaagatc   1920
tttggggccg tagaagagga cagctccctg gattcccgg tcgagggcc tggaaccagc   1980
ctcagtctcg aggccacagt catgccctac cttcaggtgt tatcagaatt ccgagaagga   2040
```

| | |
|---|---|
| gtgcggaaga ttgcccgaga gcaaaaagtc cctgagattc tgcagctcag cgatgccctg | 2100 |
| cgggacaaca tcctgcccga gcttggggtg cggtttgaag accacgaagg actgcccaca | 2160 |
| gtggtgaaac tggtagacag aaacaccttg ttaaaagaga gagaagaaaa gagacgggtt | 2220 |
| gaagaggaga agaggaagaa gaaagaggag gcggcccgga ggaaacagga acaagaagca | 2280 |
| gcaaagctgg ccaagatgaa gattcccccc agtgagatgt tcttgtcaga aaccgacaaa | 2340 |
| tactccaagt ttgatgaaaa tggtctgccc acacatgaca tggagggcaa agagctcagc | 2400 |
| aaagggcaag ccaagaagct gaagaagctc ttcgaggctc aggagaagct ctacaaggaa | 2460 |
| tatctgcaga tggcccagaa tggaagcttc cagtga | 2496 |

<210> SEQ ID NO 8
<211> LENGTH: 2226
<212> TYPE: DNA
<213> ORGANISM: Drosophila melanogaster

<400> SEQUENCE: 8

| | |
|---|---|
| atgtcgaaac gtgggcaacc ggcgtggcaa gctcccgagg cggtggatcg gccgaaactg | 60 |
| aagctgttca acagcctgac gcgacagaag gaggacttcg tgccgctgga cggcaataat | 120 |
| gtaacgtggt atagctgcgg acccaccgtc tacgatgcct cacacatggg gcatgctaga | 180 |
| tcttacattt ccttcgacat tctgcggcgc attctgtccg actactttgg ctacaacatt | 240 |
| cactatgtga tgaacattac ggacatcgac dacaagatca taaggcgtgc gcggcagaat | 300 |
| catctcttcg acgagtacgc tgctgaggcg caaaagctgc cactggatga gctgctgggt | 360 |
| cagcaaaagg aggtactgca gcggtttcag gatacatgcg ccaagaatac agatcccgac | 420 |
| aagaagatta tgctcgacaa gacactgcag cggatgaacg atgctgtgga ggcgctgacc | 480 |
| aaggccgttg gcaagggtga tgagcggag atatccgaga agcggctgct ttacctaaac | 540 |
| gaagccaagg atccaatttc cgactggttg gactcgctaa agggtgctca gatcaatgat | 600 |
| aatgcagtat ttgaggcact gccgcggtac tgggaagacc agttccacaa cgacatgaaa | 660 |
| tcgctaaata ttctcccgcc agatgtttta actcgcgttt cggagtacgt gccacaaatc | 720 |
| gtcaccttta ttcaaaagat tatcgacaat ggcttggcct atgcagccaa caactccgtt | 780 |
| tatttcgatg taaatggctt cgacaagagg gaaaagcatc attatgctaa gctggtgcca | 840 |
| gaagcatatg cgacaccaa gtccctgcaa gaaggtgaag gcgatctgtc catcgcagag | 900 |
| gatcgtctct ccgagaagcg ttctgccaat gactttgcct tgtggaaggc gagcaaagcc | 960 |
| ggcgaaccct ggtgggatag ccctggggc aagggccgtc caggctggca cattgaatgc | 1020 |
| tcggccatgg cctcggatat cttttgggccc acgtttgata tacacactgg cggtgtggac | 1080 |
| ttaaagttcc ctcatcacga caacgagctt gcccaatcgg aggccgcttt taatgagtcg | 1140 |
| gagtgggtta agtacttcct gcacacgggt cacctcacca tagctggctg caagatgtcc | 1200 |
| aagtcgctga gaactttgt caccatccag gaagctctta aaaagcattc cgccacccag | 1260 |
| ctgcgactgg cgttcctgct acactcgtgg aaggatactc ttgactactc agaaaacacc | 1320 |
| atggaaatgg ccacccaata cgaaaagttc ctcaatgagt tcttcctgaa tgtcaaggat | 1380 |
| ctgacgcggc atgtgctctc cgaagagccc cgccggcagt tgatgcctg acagaagtt | 1440 |
| gaggcggctt tgcagaagaa attctcaaat gctcaggtcc aagtacacgc cagcttgtgt | 1500 |
| gacaacatg atactcgcag cgcccttgac gccattcgag agctggtatc cgtgtccaat | 1560 |
| gtctacattc gcgacaataa gactagactc aacagtctgc tgctccgaaa cgtagccaca | 1620 |
| tatatcaccg atctgttgca cgtgtttggc gcaatatctg gtcctcgcgg tggcattggc | 1680 |

```
ttccccgtta gtggtggctc gggagcacaa gctgccggcg cggatttaga aactacggtt    1740
ttgccttacg ttcaatcgct ggctgaattc cgctacttgg tgcggagcaa agccaaaact    1800
ctgaaggcct tcgacatcct gaagctctgc gatgatctac gcgacaatgt gctgcccaat    1860
ttgggcgtgc gactggagga caaggatatt ggaaagtatg ccgtaaagct agtcgaccgc    1920
gactcacttt tacgagaacg ggaggcaaag ctggccgccg aagcggagaa ggcagcagaa    1980
aaggagcgca agaagcaggc ggctgcggag gctgcagctg cgaaagaagc ccagcgacgt    2040
gtgaatccca aggaaatgtt cctggccgaa accgaaaagt actcagcgtt cgacgaaaat    2100
ggccttccca ctcacgacaa ggagggcaaa gaagtcagta aggacagat caagaagctg    2160 cagaaactcc aacagcagca ggaacagcgt tacaatgagt atttggcatc aattgagaaa    2220
gcctga                                                               2226
```

<210> SEQ ID NO 9
<211> LENGTH: 2475
<212> TYPE: DNA
<213> ORGANISM: Danio rerio

<400> SEQUENCE: 9

```
atggcaagcg caggagacgc agcctttgat tatggcttct tattgcgcat aagtgaggat     60
tctcgcttgg ttgaggctct gaatgagtac ttgagcagtc gcagttacct ggctggctac    120
gggccctcgc aggcggacgc agaagccttt gcgcttctct gcaggccccc acctgagcgc    180
catgtccatg ccctgcgctg gtacaaaaca atagccttcc tgaagcccca agccaatgac    240
cagagcccag aatgcagcac gaagggaaaa cgggtgcagc accatggtc tcctccagag    300 ggaacagaca tttcaaagct acgtctttac aacagcctca cgcgcaccaa ggaggtgttt    360
gtaccgcaga agggcaaccg ggttctgtgg tactgctgcg gccccacggt gtatgacgct    420
tctcacatgg gtcacgccag gtcctacatt tcttttgaca tacttaggag aatactgaag    480
aactatttca gtatgacgt cttctactgt atgaacatca cagacattga tgacaaaatc    540
atcaaaagag ctagacagaa ttacctgctg gagcagtaca gagagaagaa gcccagtgcc    600
gctcagatcc tgcaggatgt gttaacagcg cgaactcctt ttaaagccaa gcttgctgag    660
actactgacc cagataagaa gcagatgctg gagagactag attcagcagt agatgccgct    720
ctgggtcccc tgcaggtggc agtgcaaagc aaggctgcgc aggattcaat tcagaagcag    780
gcacaggtct tactggagga ggccaaggat cttctgtcag attggttaga ctcgcagttt    840
gggagccagg tgacagaaaa ctccatattc tctttactgc caaagtactg ggaaggagag    900
taccataaag acatggaagc cctgaatgtc cttcctcctg atgtactcac acgggtcagt    960
gagtacgtac cagagattgt ggagtttgtc aaaaagattg tggacaatgg ttatgggtat   1020
gagtccaatg gatctgtata ttttgacacg gcaaagtttg attcttgccc tgctcactct   1080
tatgccaagc tggttccaga ggctgtgggc gatcagaaag ctcttcagga gggagaagga   1140
gacttgagca tctcagcaga tagactcagt gagaaaagat cacagaatga ctttgcattg   1200
tggaaggcct ctaagcctgg ggaaccatcc tgggactccc cttggggaat ggggagacct   1260
ggttggcata ttgagtgttc tgccatggcc ggatccatac taggagaatc tatggatatc   1320
cacggaggag gatttgactt acgttttcct catcatgaca atgagctggc gcaatctgag   1380
gcctactttg agaatgatta ctgggtacga tatttcttgc acacgggtca cctcaccatc   1440
gccggatgca aaatgtccaa atctctgaag aactttatca ccatcaaaga tgccctggcc   1500
```

-continued

| | |
|---|---|
| aaacatacag caagacaact tcgtttggcc tttctgatgc attcatggaa ggacacatta | 1560 |
| gattattcca acaacacaat ggagtcagcc atccaatatg agcgattcat aaatgagttc | 1620 |
| ttcctaaatg ttaaagatat tctgaggagc cctacagaca tcactggcca atatgagaaa | 1680 |
| tgggaagctg aggagattga actgaacaaa tgcttctatg caagaaaaac atcagttcat | 1740 |
| ggggcgctgt gtgataacat agacactcgt tcagctctgg aggagatgcg ggctcttgtt | 1800 |
| ggtcaaagca acacctacat ggctgccagg aggagtgcaa aactaccacc aaaccgcatg | 1860 |
| ctgctacaga gcatcgccct gtacttgact gacatgttga agacatttgg agcgattgag | 1920 |
| ggaaccgacc cgattggctt ccccgttgga ggaaacggac agagcgctga tctggagagc | 1980 |
| acagtcatgc cctatttgtc agtgctgtcc gatttcaggg aagacgtcag gaaaattgca | 2040 |
| agagagaaga aagtcactga attgctgcag ctttgtgacc aattgcgcga cgatacttta | 2100 |
| cctgagctgg gggtccgact ggaggatcgt gatgggctcc ccacatcggt gaagttggtg | 2160 |
| gacaaagaaa cacttctgaa agaaaaagaa gaaaagaaaa agctgaagga cgacaagaga | 2220 |
| aagaaaaaag aagaggctgc aaggaagaaa caagaacaag agatggcaaa gttggcaaag | 2280 |
| atgaagctta aacctagtga aatgttccgg tcagagactg acaagtactc cagctttgat | 2340 |
| gaaacgggct tcccgacaca tgatgctgag ggaaaggagc tcagtaaggg actgaccaag | 2400 |
| aagctgcgta agctttacga gactcaggag aagctgcata cgaataccct ccagtcaact | 2460 |
| cagaacggga gctga | 2475 |

<210> SEQ ID NO 10
<211> LENGTH: 2304
<212> TYPE: DNA
<213> ORGANISM: Saccharomyces cerevisiae

<400> SEQUENCE: 10

| | |
|---|---|
| atgaatatct tcataaaagc cctgagaaga tatactataa tgtctacgcc gaagattgtg | 60 |
| cagcccaaat ggaaggttcc aacgccacaa gctaaagaaa ctgtgttgaa gttgtacaac | 120 |
| agtttaacaa gatctaaggt tgaattcatt ccgcaatctg caatagagg tgtcacttgg | 180 |
| tactcttgcg gtcctactgt ttacgatgcc tcccatatgg gtcatgccag aaactatgtc | 240 |
| tctattgata tcaatagaag aattattcaa gattattttg gttacgacgt gcaatttgtg | 300 |
| caaaatgtta ctgatatcga cgataaaatt attttgagag ctagacaaaa ctatttattt | 360 |
| gacaattttg tcaaagaaaa tgataccaaa ttcaacgcca ctgttgttga caaggtcaaa | 420 |
| accgcacttt tccaatatat caacaaaaat tttactattc aaggcagcga gatcaaaact | 480 |
| atcgaagaat ttgaaacttg gttatcgaat gctgatactg aaactttaaa attggagaat | 540 |
| cctaaattcc ctatgcatgt caccgcagtt caaaatgcta ttgaatcaat cactaagggc | 600 |
| gattccatgg acgcagaagt tgcctttgaa aaagtcaagg acgttacggt tcctctattg | 660 |
| gataaagaat tgggctctac cattagcaat ccagagattt tccgccaact tccagcttac | 720 |
| tgggaacaga aattcaatga tgacatgtta tcattaaacg tgctacctcc caccgttaca | 780 |
| actcgtgttt ctgagtacgt tccagaaatt attgactttg ttcaaaaaat tattgataat | 840 |
| ggttacgcat atgccacttc cgacggttcc gtgtactttg atactttaaa atttgacaaa | 900 |
| tccccaaatc atgactatgc taaatgccag ccatggaata agggccagtt agacttaatt | 960 |
| aatgatggtg aagggtcctt aagcaacttt gctgataacg aaaaaagtc gaataatgat | 1020 |
| tttgctttat ggaaggcttc caaggcaggt gaacctgagt gggaatcacc atgggtaag | 1080 |
| ggtagaccag gatggcatat tgaatgttct gtgatggcca gtgatatcct aggctctaac | 1140 |

```
atcgatattc attcaggtgg catcgatttg gcctttcctc accatgataa cgaattggct    1200
caatccgagg ctcgcttcga caatcaacag tggatcaact atttcttaca tacgggccat    1260
ttacatattg agggtcaaaa aatgtctaaa tccttaaaga atttcattac cattcaagaa    1320
gctttgaaaa aattctcacc gcgccaatta agattggctt ttgcctcagt acaatggaac    1380
aatcaattgg atttcaagga atctttgatc catgaagtaa agtcatttga aaactccatg    1440 aacaatttt ttaagactat tagagcattg aagaacgatg cagcttctgc aggtcatatc    1500 tctaaaagt ttagtccctt agagaaagaa ttattggctg attttgttga aagtgaatcg    1560
aaagtccatt cggcgttctg tgataattta tccacacctg ttgctttgaa gacactgagc    1620
gaattagtga ccaagtcaaa cacatacatt accactgcag gtgctgcttt aaaaattgag    1680
cccttgattg ctatctgtag ctacatcacc aaaatcttaa gaataattgg atttccatcc    1740
cgtcctgaca atttggggttg ggcagcccaa gctggctcca acgatggatc cctaggctca    1800
ttggaagaca ctgttatgcc atatgttaag tgtttatcca catttagaga tgatgtacgt    1860
tccttagcta tcaagaaagc cgaacccaag gaattcttgc aattaacgga taaaattaga    1920
aacgaagatt tgctaaactt gaatgttgcc ttggatgata ggaatggaca atctgccttg    1980
atcaaatttt tgactaacga tgaaaaattg gaaattgtca agctaaacga ggagaaacat    2040
gccaacgaac tagcaaagaa acaaaagaaa ttggaacagc agaaattaag agagcagaag    2100
gaaaacgaga ggaagcagaa agctcaaatt aaaccacaag atatgttcaa ggatgtcaca    2160
ttgtacagtg cttgggacga gcaaggcctt ccaacaaagg acaaagacgg taatgatatc    2220
accaagagta tgaccaagaa gttgaagaag caatgggaac aacaaaagaa gctacatgaa    2280
gagtactttg gtgaagacaa atag                                           2304
```

<210> SEQ ID NO 11
<211> LENGTH: 1701
<212> TYPE: DNA
<213> ORGANISM: Danio rerio

<400> SEQUENCE: 11

```
atgacaatga ggctggcttc agcactgata cttaattctg gctttagaat caggcgtgaa      60
attcatagtg gagttacaaa aacgtcatta ctgtgccgtc gtactgcatg cagcaggacg     120
gaaagagggt gggtaaaacc agtgggtttt gacaccggtg taacggctta caatagtctt     180
accaagaaga aagaaccttt aattctgtca caagaaaaaa ttgctacctg gtatagctgt     240
ggaccgactg tttatgatca tgcccatctg ggtcatgcgt gttcatatgt cagatttgat     300
attctccaaa ggatattatc aagacttttt ggaattaatg tcattcatgt tatggtcatc     360
actgacattg atgataaaat catacaaaga agccttgagg agaacatctc acccatcact     420
cttgcaagaa tgcacgagga agaatttaaa aaggatatgc tagcactgcg ggttcttcct     480
cccgtagtat atatgagggt gacagaaaat atacctcaaa ttatagcttt tatagagcgt     540
attattggaa atggacatgc ctatgtcaca agtcaaggga atgtctactt taacacgaag     600
tctattagtc atcgttatgg caagcttgtc aatcttggag gaaatgctgg ggaacaggg     660 gttcaggaca aagagaattc aagagacttt gctttgtgga agcatccaa accatttgaa     720 ccttactggg agtcaccttg gggacaagga agacctgggt ggcacattga atgttccaca     780
attgctagct cagtgtttgg acatcagctg gatatacact ctggagggat tgaccttgcc     840
ttcccacacc atgagaatga aattgcccag tcagaggcat atcatcagtg tgaacagtgg     900
```

```
ggaaactact ttctacactc tgggcacctt catttaaaag gaagtgtaga gaagatgtca    960
aaatccttga agaattatgt aactataaag gattttctgg catcttatac tgctaatgag   1020
tttcgacttt tctgtcttct gaccaaatac agatcagcaa tcgactatag tgatgctagc   1080
atgaatgaag cccaatctac actgtccacc atctctgcct tcttccacaa tgcacaggcc   1140
tacatgcagg gccacatgca gtgccagcct gtagaggaag gatttctctg ggagaggttg   1200
tctaatactc agaccagtgt tcataaaatg cttgccgatg actttgacac accaaaagct   1260
gtggatgcca tcatgagtct catttaccat ggcaactgtc agcttcagcc tgctactaag   1320
gtggatgggc ctaggagtcc tgctgtattt ggagccataa tgtcctatgt tatggaaata   1380
atgagtgttt ttggagtgga tctatcagac aaaacggaag tccaagtttc ctctggagtt   1440
ttgaataatg ttgtggagga gttggttcat tttcggagtg aagttcgtaa atttgctctt   1500
tctgtggaag accaagcacc acaggaatcc cagactggca ataaaaatca gaaaaggcat   1560
catcaaccag acagattaca cttaagctta ctgaaagcgt gtgatgcctt aaggaataat   1620
ctagcacccc ttggagtcca cattaaggat agaggcacca actccacgtg ggaggtaaca   1680
aaggcagaga cgaggaagta g                                             1701

<210> SEQ ID NO 12
<211> LENGTH: 1677
<212> TYPE: DNA
<213> ORGANISM: Drosophila melanogaster

<400> SEQUENCE: 12
atgtatagcc tcaaggaggg gctccgggct cttaacagtc gaacgagacc agctctcatt     60
tgccggcgca acatttcgga ggaggctccc aaacaggata gtccgtttaa atggagaaaa    120
ccaattggcc agcacacagg aatcaatata tacaatcacg gcttgcggca gaaggtaccc    180
ctaatcctac gcaatcccca aatggtcaca tggtacactt gcggacccac tgtttatgac    240
tccgcgcacc taggtcatgc cagcacctat gtcaaggtag acatcctgca gcgcattctc    300
cgcgattatt ttaaaatcaa cctggtgaca gccatgaaca tcacggatgt tgacgacaag    360
atcattaagc gggcccagct cgctggactg gactggcaga gatggcgcg agcttatgaa     420 gcggaatttc gtcaggacat gttgcgtctc aatgttcagg cgccggatgt gcgcagtcat    480
gtgactacca ccatgcctgt cattattcag ttcattcagc agctgataga cggaaagcag    540
gcttacgtta ccccggataa ctctgtttac tttgatgtct ccaaaagcaa gaactatgga    600
aagcttcaaa acttaggcct aagcgaggac aaattggacc ccatcaaacg aaacactgcc    660
gattttgcct tgtggaaggc gcgtaaaagt ggcagtgagc ccacgtgggc tgcaccctgg    720
ggtggcgagg gacgccccgg ttggcacatt gaatgcagcg ccattgcagg tttattcttt    780
ggccgccagt tggacattca tgctggcggc ttggacttgc gttttccgca ccacgaaaac    840
gaggaggcgc agtgctgtgc acggtataaa actgaccagt gggtaaacta ttgggtgcac    900
accggacaac ttcatatggt tggagatcgg agaagatgt caaagtctct gggcaacacg     960
atctccgtgt cggagctgct gaagaagtac accgccgatg agtttcgaat ggcctgcctg    1020
ctgtccaatt accgcaatgc aatgcctttat agcgatcagt tgatggtgac ggctcgccag   1080
accctgcagc ggtttagaaa cttccaggcc gatctaagtg cctataccca attcctgaag   1140
```

| | |
|---|---|
| cccgtgcact tgttagacga gggagcgtta aaggcccaac tgactcatac agtaaccgaa | 1200 |
| ttcgataatt gccttcgaga tgatttcgat accgccagag ccatcagcgt gctaatcgat | 1260 |
| cagatgagca gcataagtcg ctgcataaat gagcagcaag tggacgcaca ggaggagccc | 1320 |
| gcctactgca ttgatctgct gttggcagct ggaaacttca taaaccgtgc catagtcacg | 1380 |
| tttggtctat cagagttgca ggataaagaa tcgttgcaag aaaaggtttc ctttacggat | 1440 |
| catagcattg atcccaattt gcttgtgaat gatgtgataa acgttcgggg aagaatgcgg | 1500 |
| gaaagggcca cctccggaaa tgttaagaac ccgcagcttt tagccgcctg tgatgaactg | 1560 |
| aggagcttgt tacaacagca cggcattcag gtccgcgacc acaaacaggg cagctcctgg | 1620 |
| gtgtttgccg tgtcctgtga aaagcaagat gataaaagca aagctctgc cgaataa | 1677 |

<210> SEQ ID NO 13
<211> LENGTH: 24
<212> TYPE: DNA
<213> ORGANISM: Artificial Sequence
<220> FEATURE:
<223> OTHER INFORMATION: Synthesised

<400> SEQUENCE: 13
cacctgggcc ttgggcgggc tggg              24

<210> SEQ ID NO 14
<211> LENGTH: 24
<212> TYPE: DNA
<213> ORGANISM: Artificial Sequence
<220> FEATURE:
<223> OTHER INFORMATION: synthesised

<400> SEQUENCE: 14 aaacccagc ccgcccaagg ccca              24

<210> SEQ ID NO 15
<211> LENGTH: 20
<212> TYPE: DNA
<213> ORGANISM: Artificial Sequence
<220> FEATURE:
<223> OTHER INFORMATION: synthesised

<400> SEQUENCE: 15
ggacagatcc agcgaacagg              20

<210> SEQ ID NO 16
<211> LENGTH: 20
<212> TYPE: DNA
<213> ORGANISM: Artificial Sequence
<220> FEATURE:
<223> OTHER INFORMATION: synthesised

<400> SEQUENCE: 16
aataatcaag agagctaacg              20

CYSTEINE POLYSULFIDATION AND MITOCHONDRIAL BIOENERGETICS REGULATED BY CYSTEINYL-TRNA SYNTHETASE

CROSS REFERENCE TO RELATED APPLICATIONS

This application is a Continuation application of the U.S. patent application Ser. No. 17/188,982 filed on Mar. 1, 2021 (as 982 application), which is a Continuation application of the U.S. patent application Ser. No. 16/655,553 filed on Oct. 17, 2019 (as 553 application). These 982 and 553 applications claim priorities of U.S. Provisional applications No. 62/747,229 filed on Oct. 18, 2018 and No. 62/911,632 filed on Oct. 7, 2019 under 35 U.S.C. § 119(e). The entire contents of the 982 and 553 applications and these Provisional applications are hereby incorporated by reference.

REFERENCE TO AN ELECTRONIC SEQUENCE LISTING

The content of the electronic sequence listing (2023-07-06-Seq-Listing; Size: 29,011 bytes; and Date of Creation: Jul. 6, 2023) is herein incorporated by reference in its entirety.

TECHNICAL FIELD

The invention is related to cysteine hydropersulfide (CysSSH) and mitochondrial bioenergetics.

BACKGROUND

Cysteine hydropersulfide (CysSSH) is found physiologically in prokaryotes, eukaryotic cells, and mammalian tissues[1,2]. Previously, we unequivocally verified the presence of remarkable amounts of CysSSH, glutathione persulfide (GSSH), and longer chain sulfur compounds (polysulfides, including CysS/GS-(S)n-H) in cultured cells and tissues in vivo in mice and humans[3-6]. The chemical properties and abundance of these species suggest a pivotal role for reactive persulfides (i.e., compounds containing an-SSH group) in cell-regulatory processes. Researchers proposed that CysSSH and related species can behave as potent antioxidants and cellular protectants, and may function as redox signaling intermediates[3-10]. Persulfides are also essential structural components of several proteins and enzymes, e.g. serving as metal ligands in iron-sulfur clusters (or sulfide donors) and in iron-cysteine and zinc-cysteine complexes[11-15]. In fact, the existence of a cell reservoir for sulfane sulfur (sulfur-bonded sulfur atoms with six electrons), including low-molecular-weight (LMW) and protein-bound cysteine polysulfides, has long been known[1,3-7,15,16]. Thus, although the prevalence of endogenous polysulfides is clearly established and their biological relevance increasingly being recognized, the chemical biology and physiological functions of these species are not known with any certainty. Current dogma holds that persulfide/polysulfide formation arises as a result of hydrogen sulfide (H2S) oxidation[3,4,7-9] or chemical reaction with nitric oxide[3,17]. Two H2S-generating enzymes involved in sulfur-containing amino acid metabolism—cystathionine γ-lyase (cystathionase, CSE) and cystathionine β-synthase (CBS)—can catalyze CysSSH biosynthesis using cysteine (CysSSCys) as a substrate[3,4,6-10,18-21]. However, the observed Km is high, and both cells and mice lacking CSE and/or CBS still display appreciable levels of CysSSH[20-24], which suggests the possibility that alternative processes may be responsible for endogenous persulfide production. Thus, it appears that other biosynthetic routes of CysSSH formation exist that have yet to be identified.

SUMMARY

This study reveals that cysteinyl-tRNA synthetases (CARSs), in addition to their canonical role in protein translation, act as the principal cysteine persulfide synthases (CPERSs) in vivo. CARSs play a novel and prominent role in endogenous production of both LMW polysulfides and polysulfidated proteins that are abundantly detected in cells and in mice. Notably, CARS2, a mitochondrial isoform of CARS, is involved in mitochondrial biogenesis and bioenergetics via CysSSH production. Based on the discovery, the present invention is related to a method of synthesize cysteine hydropersulfide (CysSSH), including taking a substrate L-cysteine and performing a reaction catalyzed by cysteinyl-tRNA synthetases (CARSs).

DETAILED DESCRIPTION OF EMBODIMENTS

Figure 1:
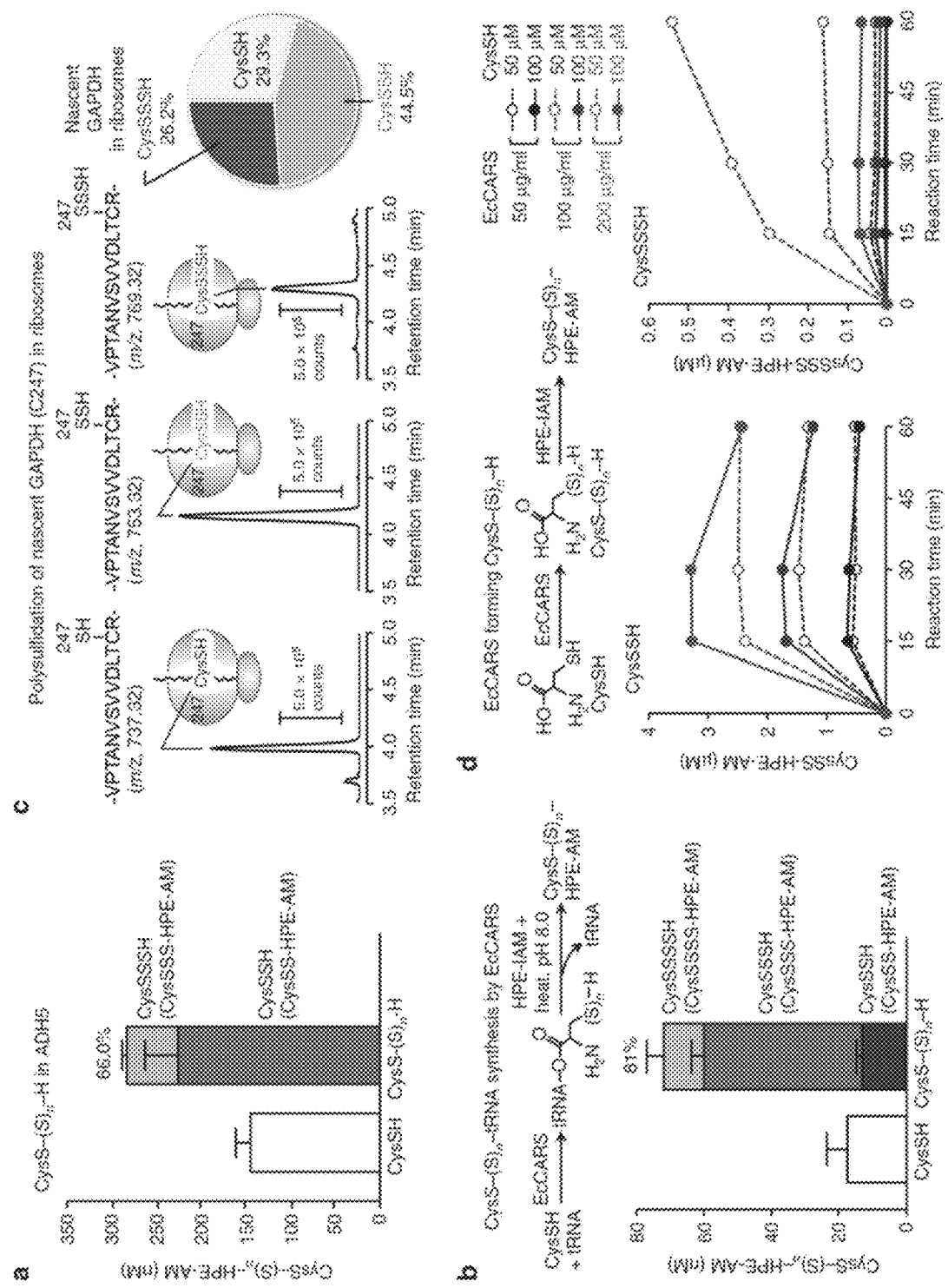
FIG. 1 shows formation of cysteine persulfide (CysSSH) and CysS-(S)n-H.

The preferred embodiments of the invention are described hereinafter.

[Principal Embodiment]

Result

Redox property of cysteine and protein polysulfides. CysSSHhas unique redox-active properties that distinguishes it from the cysteine (CysSH) thiol. In evaluating the physiological rationale for biological CysSSH production, our present study confirmed that cysteine persulfide/polysulfides (CysSSH/CysS-(S)n-H) possess mixed sulfur reactivity-both nucleophilic and electrophilic (Supplementary FIGS. 1 and 2)—a property that is unique and distinct from that of other simple biologically relevant thiols. The dual electrophilic-nucleophilic character of hydropersulfides is well documented (the anionic RSS— species being nucleophilic and the protonated RSSH species possessing electrophilic properties akin to disulfides, RSSR)[25-27]. Moreover, dialkylpolysulfides can also be nucleophilic and electrophile-mediated cleavage of S—S bonds is established[28]. The unique properties and reactivity of polysulfides allowed us to develop several analytical techniques aimed at determining endogenous production of LMW and protein-bound polysulfides (Supplementary FIG. 3). We first developed a convenient method for selective detection of polysulfidated proteins: the biotin-polyethylene glycol (PEG)-conjugated maleimide (biotin-PEG-MAL) labeling gel shift assay (PMSA; Supplementary FIG. 3a)15. PMSA demonstrated extensive protein-bound cysteine polysulfidation (Supplementary FIG. 4), not only for recombinant proteins, prepared in an *Escherichia coli* cell expression system (Supplementary Table 1) but also for endogenous proteins expressed in mammalian cells. We then used liquid chromatography-electrospray ionizationtandem mass spectrometry (LC-ESI-MS/MS) with 0-(4-hydroxyphenyl) ethyl iodoacetamide (HPE-IAM) as a trapping agent to identify and precisely quantify various hydropolysulfides, and also to verify the site specificity of polysulfidation as well as the number of sulfur atoms involved in proteins (Supplementary FIG. 5, and Supplementary Table 2). We chose HPE-IAM for the LC-ESI-MS/MS analyses, as described recently6 because of its mild electrophilicity that ensures specific labeling of hydropolysulfides to form stable adducts without appreciable artifactual decay related to their dual nucleophilic and electrophilic character (Supplementary FIG. 2). In fact, we quantified CysS-(S)n-H formed in alcohol dehydrogenase 5 (ADH5) and glyceraldehyde-3-phosphate dehydrogenase (GAPDH) by LC-MS/MS analysis, after pronase digestion of the HPE-IAM-labeled proteins, which revealed that more than 70% of cysteine residues were polysulfidated (FIG. 1a and Supplementary FIG. 6), a result consistent with the PMSA profile alluded to above (Supplementary FIG. 4). The treatment of ADH5 with N-ethylmaleimide (NEN) indeed completely abrogated the HPE-IAM labeling of CysSH and CysSSH/SSSH as evidenced by LC-ESI-MS/MS analysis shown in Supplementary FIG. 6b. This data indirectly supports the electrophilic decomposition of protein-bound cysteine polysulfides induced by a strong electrophile NEM. Additional LC-quadrupole (Q)-time-of-flight (TOF)-MS analyses identified sites of polysulfide formation and the sulfur chain length in each protein (Supplementary FIG. 7).

Figure 9:
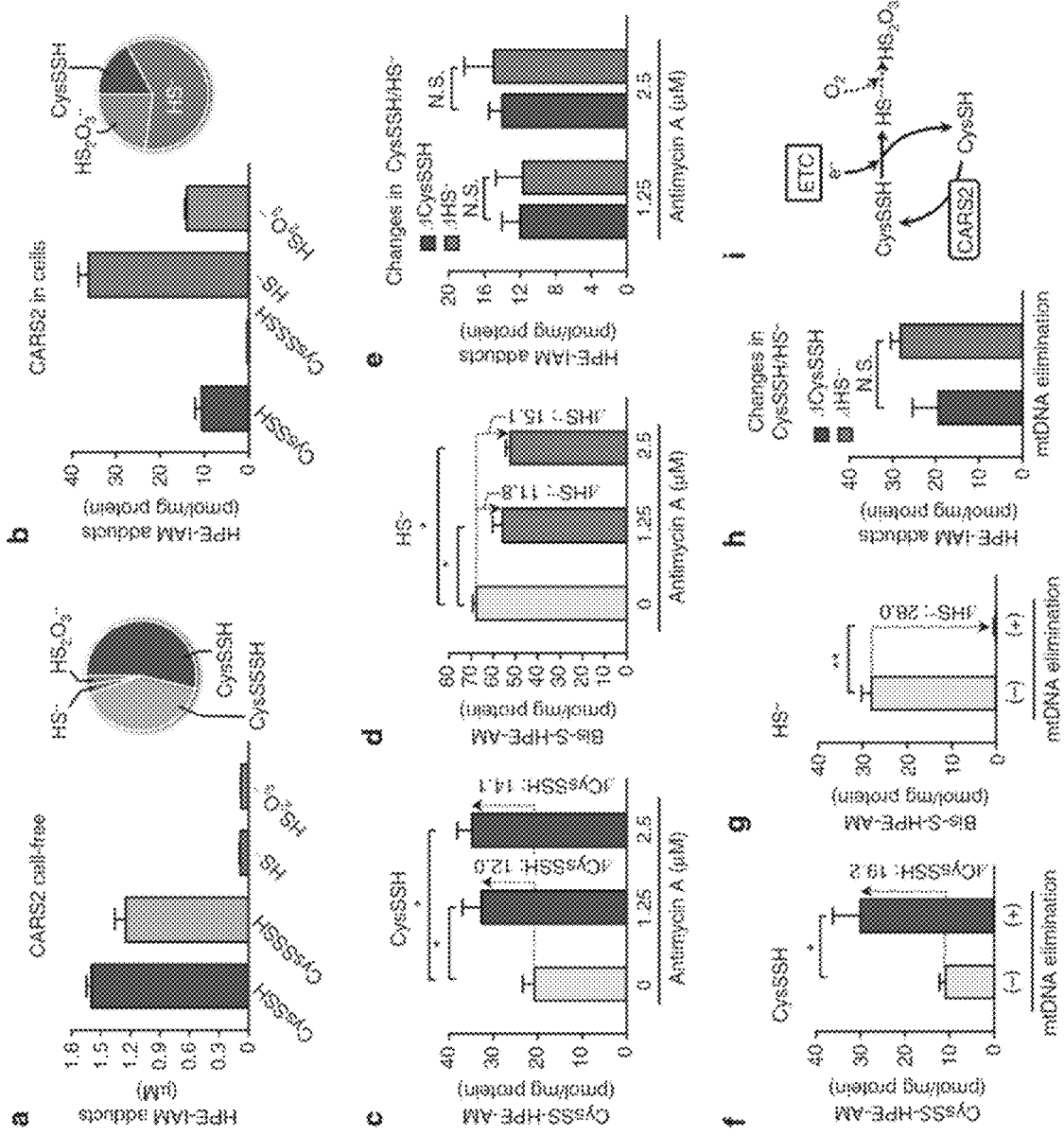
FIG. 9 shows Mitochondrial ETC-mediated reduction of CysSSH.
Figure 10A:
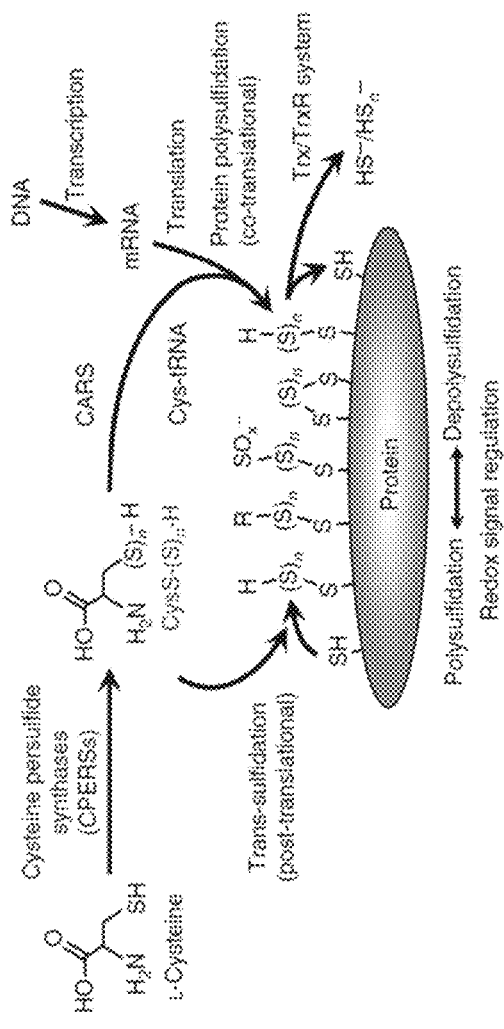
FIGS. 10A and 10B show CARS-mediated protein polysulfidation and mitochondrial functions.
Figure 10B:
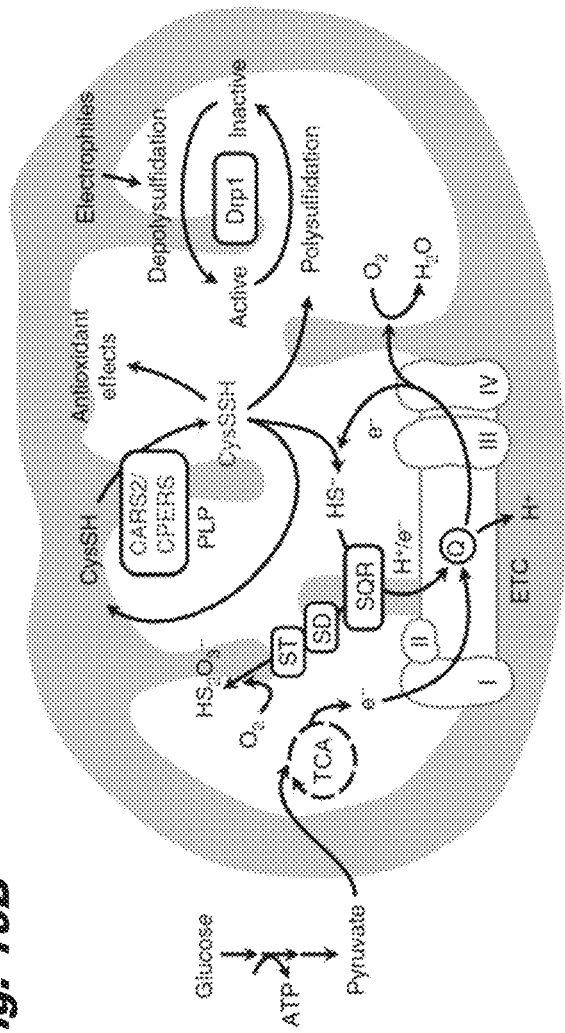

Protein polysulfidation induced by cysteinyl-tRNA synthetase. Because such extensive protein polysulfidation is unlikely to occur effectively by simple chemical means3,4, 7-10, we hypothesized that CysSSH and CysS-(S)n-H may be incorporated during protein translation. To evaluate this hypothesis, we analyzed the incorporation of CysSSH/CysS-(S)n-H into tRNA via cysteinyl-tRNA synthetase (CARS) from *E. coli* (EcCARS) by using synthetic CysS-(S)n-H and LC-MS/MS analyses (Supplementary FIG. 8). We observed effective production of CysSSH-bound tRNA (CystRNA-CysSSH), which indeed suggests translational incorporation of CysSSH/CysS-(S)n-H into proteins. Unexpectedly, we identified extremely high levels (>80% of total cysteine residues) of tRNA-bound cysteine persulfide, trisulfide, and even tetrasulfide, when using simple (native) cysteine with EcCARS (FIG. 1b and Supplementary FIG. 9). As an important result, these cysteine polysulfides bound to tRNA were effectively incorporated into nascent polypeptides, which is synthesized de novo in the ribosomes (FIG. 1c), as verified by a modification of the puromycinassociated nascent chain proteomics (PUNCH-P) method29, here termed PUNCH-PsP, PUNCH for Polysulfide Proteomics (FIGS. 10A and 10B). This PUNCH-PsP analysis allowed us to obtain specific and selective identification of the intact forms of CysS-(S)n-H residues in the nascent peptides of GAPDH present only within the ribosomes of *E. coli*, as FIG. 10A shows. We clearly identified high degrees of polysulfidation occurring at the 247Cys residue of the mature GAPDH protein expressed and synthesized in *E. coli*. All native forms of CysSH, CysSSH, and CysSSSH residues were efficiently recovered from the native whole GAPDH protein and the extension of polysulfidation reached more than 60% of the 247Cys residue of mature protein. All these rigorous LCQ-TOF analyses unambiguously revealed that extensive and prevalent cysteine polysulfidation is introduced co-translationally and sustained in the mature protein physiologically present even in the post-translational processes of the cells. Consistent with these findings, EcCARS itself appeared to have strong catalytic activity for generating CysS-(S)n-H (CysSSH and CysSSSH) from the natural substrate cysteine (FIG. 1d). The persulfide synthase activity of EcCARS depended partly on added pyridoxal phosphate (PLP) (FIG. 2a) but not on ATP and tRNA: the latter two being required for Cys-tRNACys biosynthesis by EcCARS. Persulfide generation by EcCARS was enantioselective, because only L-cysteine but not D-cysteine demonstrated activity, which ruled out nonspecific post-translational persulfidation. Furthermore, we performed a stable isotope (34S) tracer experiment combined with LC-MS/MS-based HPE-IAM assay to clarify the catalytic mechanism of cysteine polysulfidation by EcCARS. Specifically, by means of LCMS/MS analysis for the enzymatic reaction with stable isotope (34S)—labeled cysteine as a substrate, we found that EcCARS catalyzed the cleavage of a sulfur atom from one cysteine and its transfer to another cysteine to form CysSSH. About the features discussed in this paragraph, a paper "W. CHEN et al, Rational Design of a Dual-Reactivity-Based Fluorescent Probe for Visualizing Intracellular HSNO, Angewandte Chemie, Sep. 3, 2019, page 16067-16070," is incorporated by reference. Prevalent cysteine polysulfidation is introduced co-translationally and sustained in the mature protein physiologically present even in the post-translational processes of the cells.

Consistent with these findings, EcCARS itself appeared to have strong catalytic activity for generating CysS-(S)n-H (CysSSH and CysSSSH) from the natural substrate cysteine (FIG. 1d). The persulfide synthase activity of EcCARS depended partly on added pyridoxal phosphate (PLP) (FIG. 2a) but not on ATP and tRNA: the latter two being required for Cys-tRNACys biosynthesis by EcCARS. Persulfide generation by EcCARS was enantioselective, because only L-cysteine but not D-cysteine demonstrated activity, which ruled out nonspecific post-translational persulfidation. Furthermore, we performed a stable isotope (34S) tracer experiment combined with LC-MS/MS-based HPE-IAM assay to clarify the catalytic mechanism of cysteine polysulfidation by EcCARS. Specifically, by means of LCMS/MS analysis for the enzymatic reaction with stable isotope (34S)—labeled cysteine as a substrate, we found that EcCARS catalyzed the cleavage of a sulfur atom from one cysteine and its transfer to another cysteine to form CysSSH. About the features in this paragraph, a paper "W. CHEN et al, Rational Design of a Dual-Reactivity-Based Fluorescent Probe for Visualizing Intracellular HSNO, Angewandte Chemie, Sep. 3, 2019, page 16067-16070," is incorporated by reference.

Identification of CARSs as CPERSs. Kinetic analyses confirmed that, because of a very low Michaelis constant Km and high cat-alytic rate constant kcat, EcCARS is very efficient in producing CysSSH, i.e., functioning as a CPERS, with a high affinity for cysteine(Supplementary Table 3), in particular when compared with the kinetic parameters of other enzymes such as CSE (Supplementary Table 3)7,21. About the features in this paragraph, a paper, "NISHIMURA et al, Mitochondrial cysteinyl-tRNA synthetase is expressed via alternative transcriptional initiation regulated by energy metabolism in yeast cells, Journal of Biological Chemistry (JBC), Volume 294, Issue 37, P13781-13788, Sep. 13, 2019," is incorporated by reference. Although the kcat/Km value is almost equal to values of EcCARS, CSE, and CBS utilize only cystine (but not cysteine) as a substrate, which is quite distinct from CARSs that use cysteine (but not cystine) for CysSSH production3. In addition, because the intracellular cystine content range is physiologically at low micromolar or sub-micromolar concentrations, which are far lower than the Km value of CSE (more than 200 μM), CSE cannot directly utilize cysteine for persulfide production. Also, the cystine/CSE reaction may not compete successfully with the reactions with other enzymes metabolizing cystine and substance such as glutathione, which exists abundantly in cells and thus readily interacts with cysteine under physiological conditions. The intracellular cysteine concentration is reportedly 100-1000 μM in cells and major organs3, which is much higher than the Km of CARS. These biochemical reports, therefore, strongly suggest that CARS can function as a major source of CysS-(S)n-H generation under physiological conditions.

Investigation of EcCARS PLP-binding sites with LC-Q-TOFMS analysis and Mascot data searches indeed revealed that lysine (K) residues, including 73KIIK76 and 266KMSK269 motifs, bound to PLP. About the features in this paragraph and the next pragraph, a paper, "M. FEELISCH, Long-lasting blood pressure lowering effects of nitrite are NO-independent and mediated by hydrogen peroxide, persulfides, and oxidation of protein kinase Glu redox signalling, Cardiovascular Research, 1 Jan. 2020, Pages 51-62, Volume 116, Issue 1," is incorporated by reference. The sequence data showed that several Lys residues, especially at the KIIK and KMSK motifs, are conserved in EcCARS and other homologues from different organisms, including mammals (FIG. 2b). Also, conserved two cysteine residues bound to the active center $Zn^{2+}$(FIG. 2b). About the feature(s) discussed here, a paper, "A. NISHIMURA et al, Depolysulfidation of Drpl induced by low-dose methylmercury exposure increases cardiac vulnerability to hemodynamic overload, Science Signaling, Vol. 12, Issue 587, 25 Jun. 2019," is incorporated by reference. To clarify the function of PLP bound to EcCARS, we constructed a series of Lys mutants of this enzyme (Supplementary Table 4) and measured enzyme activities in terms of persulfide, i.e., CysS-(S)n-H, formation and protein synthesis or translation. We observed, via the HPE-IAM labeling LC-MS/MS analysis, a marked decrease in CysSSH and CysSSSH synthesis, compared with the wild type (WT), for various Lys to Ala mutants at K73A, K76A, K266A, K269A, and double mutants K73/76A and K266/269A of EcCARS (FIG. 2c), all of which had intact protein synthesis potential as assessed by the PUREfrex cell-free protein synthesis assay (FIG. 2d). We also quantified the amounts of PLP bound to EcCARS by LC-ESI-MS/MS using 2,4-dinitrophenylhydrazine (DNPH). The DNPH-labeling LC-MS/MS analysis indicated that the amounts of PLP bound to WT EcCARS and four different Lys mutants correlated well with their CPERS (persulfide producing) activities. In contrast, cysteine to aspartate mutants such as C28D (also C28S) and the double C28/209D mutant still maintained high persulfide production, similar to that of the WT cells (FIG. 2e), albeit their protein synthesis and translational activity were strongly attenuated (FIG. 2f).

Our computational modeling of the three-dimensional struc-ture of EcCARS supported PLP binding to the particular Lys residues at the 73KIIK76 and 266KMSK269 motifs of EcCARS (FIG. 3a). The present computational simulation predicts two potential PLP-binding sites at K73 and K269 of KIIK and KMSK motifs. Also, this modeling revealed that PLP-bound motifs have a vicinal location within 10-20 A distance but apparently distinct from both the ATP-binding HIGH motif and the Zn2+-binding active site of the EcCARS for Cys-tRNACys biosynthesis. A commensurate change in the binding capacity and/or stability of PLP seems to exist, caused by the mutation of any one of four Lys residue among four Lys residues because each single Lys mutation at the KIIK and KMSK motifs greatly affected all CysS-(S)n-H synthesis activity of EcCARS (FIG. 2c). One possible explanation for the commensurate effect is that PLP may need multiple Lys residues, rather than a single Lys binding, to exhibit stable binding and full catalytic activity of CARS to function as CPERS during CysS-(S)n-H formation. That is, for their stable binding and catalytic activity, PLP-dependent catalytic activity may need stabilization by a multiple Lys binding, because CysSSH produced by CARS, due to its highly nucleophilic nature, may readily interfere with the electrophilic aldehyde group of PLP to form an imine (Schiff base) linkage on the Lys residues, which would cause instability of the catalytic activity of PLP bound to these particular Lys residues of CARS. This interpretation receives support from by the aforementioned computational structural analysis showing the close localization (in 20 A) of these Lys residues at KIIK and KMSK motifs (FIG. 3a). Together these data suggest that EcCARS is indeed an efficient CPERS enzyme with independent catalytic functions in aminoacyl-tRNA biosynthesis.

CARS2 functions as a CPERS conserved in mammals. Twodifferent CARSs exist in mammals: CARS1 (cytosolic) and CARS2 (mitochondrial)30-32. Both CARSs (mouse CARS1 andhuman CARS2, which we tested herein) had strong CysS-(S)n-Hproducing activities, which depended on the presence of PLP (FIG. 3b-d). Also, a very nice correlation was found between the CPERS activity and PLP content of CARS2 containing varied amounts of PLP incorporated after treatment with different concentrations of PLP (FIG. 3e). To clarify how much cellular CysS-(S)n-H originated from CARS1 and CARS2 in human cells, we attempted to disrupt CARS1 and CARS2 genes in HEK293T cells via the CRISPR/Cas9 system in HEK293T cells. We could not obtain CARS1-knockout (KO) cells, but we successfully established CARS2 KO cells. We selected one of the clones, carrying a 30-bp deletion plus an 8-bp insertion just downstream of the translation-initiating codon in the CARS2 first exon, was selected for LC-MS/MS analysis. CysS-(S)n-H and GSSH levels decreased significantly in CARS2 KO cells (FIG. 4a, b), which suggests that CARS2 is a major producer of persulfide. Because we still detected a low level of CARS2 in CARS2 KO cells (FIG. 4c), we also treated the cells with siRNA against CARS2, which resulted in the 67 and 42% decreases in CysSSH and GSSH levels, respectively (FIG. 4a, b). When we knocked down CARS1 in CARS2 KO cells, CysSSH decreased only marginally, which suggests a predominant role of CARS2 in the production of CysSSH. Immunoblot analysis and immunostaining verified the reduced CARS2 and CARS1 protein levels in CARS2 KO cells and in cells with CARS1 or CARS2 siRNA. About the features discussed in the paragraph, three papers, "1) C. YANG et al, Data—Driven Identification of Hydrogen Sulfide Scavengers, Angewandte Chemie, 131, page 11014-11018, 13 Jun. 2019, 2) RUDYK Et al, Oxidation of PKGIα mediates an endogenous adaptation to pulmonary hypertension, PNAS, 116 (26), page 13016-13025, June 2019, and 3) M. AKIYAMA et al, Erratum: Environmental Electrophile-Mediated Toxicity in Mice Lacking Nrf2, CSE, or Both, Environmental Health Perspectives, Vol. 127 (6) June 2019" are incorporated by reference.

Markedly reduced persulfide formation in CARS2 KO cells was recovered by adding back WT CARS2. CARS2 C78/257D mutant rescued the persulfide production of CARS2 KO cells, but K124/127A, and K317/320A mutants (mutants of KIIK and KMSK motifs, respectively), did not (FIG. 4d, e). The CARS2 KO cells had a markedly decreased Cys-tRNA synthetase activity, and again adding back the C78/257D mutant resulted in lost Cys-tRNA synthetase activity, as assessed by the expression of mitochondrial cytochrome c oxidase subunit 1 (MTCO1 encoded by mitochon-drial DNA), but still retained full CPERS activity; conversely, K124/127A and K317/320A mutants had impaired CPERS functions but retained Cys-tRNA synthetase activity (FIG. 4f, g). These results clearly verify that CARS2 truly functions as a CPERS in mammals and that this function is separate from cysteinyl-tRNA synthetase activity.

We also evaluated the potential contribution of CSE and CBS to the endogenous persulfide production in HEK293T cells. Silencing of CSE and CBS suppressed the persulfide production, but notably, intracellular cysteine (CARS substrate) levels were significantly decreased. In CARS2 KO cells, knockdown of CSE and CBS also reduced cysteine levels but not persulfide production. Therefore, cysteine production is dependent on both CSE and CBS, and thus cysteine is provided via the metabolic pathways mediated by CSE/CBS in each cell line irrespective of CARS2 expression. In addition, almost two thirds of CysSSH seems to be supplied by CARS2 in HEK293T cells based on the decrease by almost two thirds in the CysSSH levels. The rest of CysSSH in the CARS2 KO cells were not derived from CSE/CBS expressed in HEK293T cells, since no further reduction of CysSSH was obtained even by CSE/CBS knockdown in CARS2 KO cells. These results suggest that CSE and CBS do not contribute directly to persulfide production but rather may promote the biosynthesis of cysteine and its supply to CARS, at least in this cultured cell model under physiological conditions. About the features discussed in the paragraph, a paper, "Y. KYOGOKU et al, Nitrosative stress in patients with asthma-chronic obstructive pulmonary disease overlap, Journal of Allergy and Clinical Immunology, 2019," is incorporated by reference.

Figure 5:
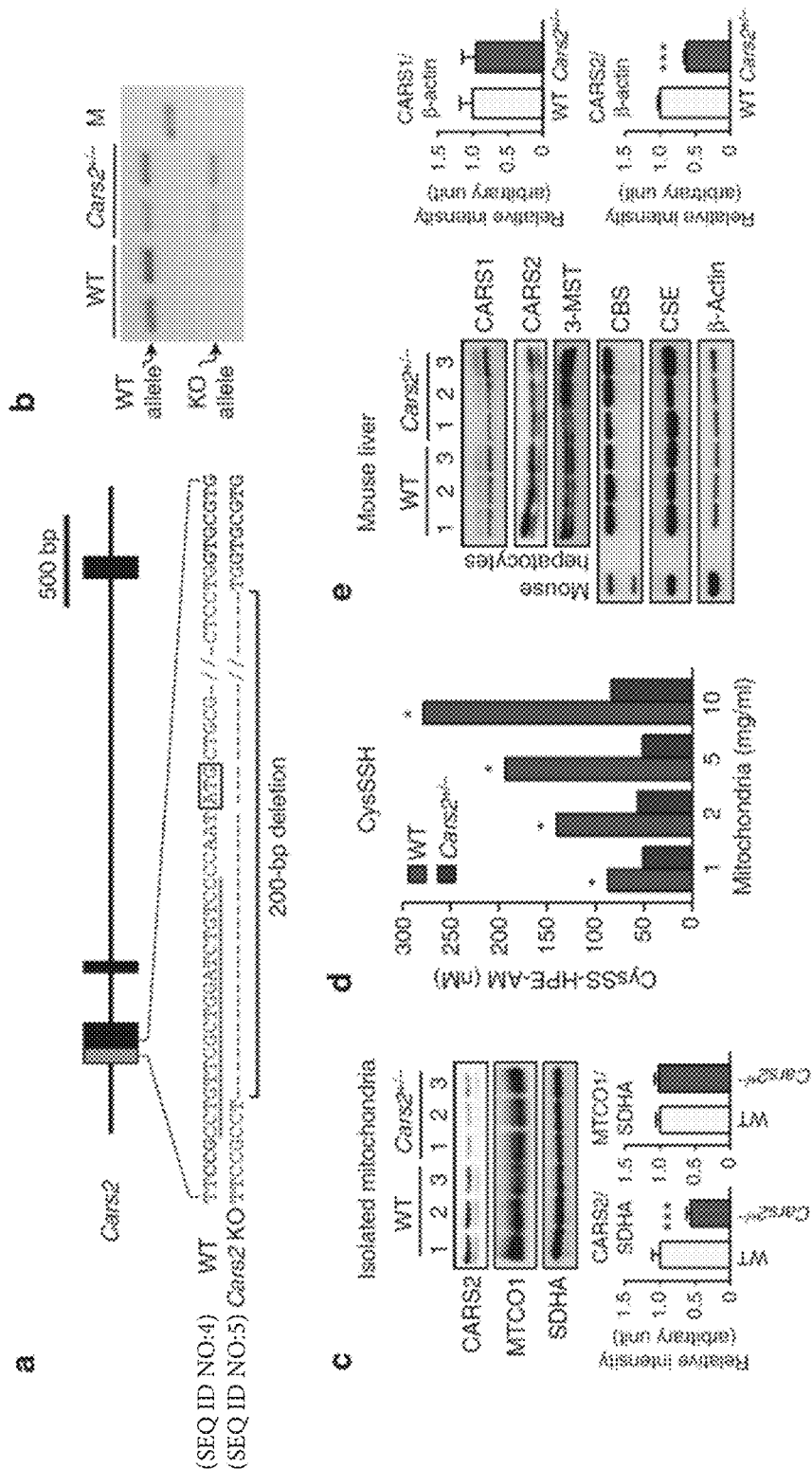
FIG. 5 shows generation of Cars2-deficient mice via the CRISPR/CAS9 system.

To further clarify CPERS functions of CARS2 in vivo, we generated the Cars2-deficient mice by using CRISPR/Cas9 technology. As FIG. 5 illustrates, a guide RNA (gRNA) was designed against exon 1 of Cars2. We established a mutant mouse line with a mutant Cars2 allele (line 1) that had a 200-bp deletion containing a translation-initiating codon in exon 1 (FIG. 5a, b). Mating of F1 Cars2 heterozygous KO (Cars2+/−) mice produced WT and Cars2+/− mice, but not homozygous mice (viable offsprings included 20 WT mice and 19 Cars2+/− mice), which suggests that Cars2−/− mice are embryonic lethal. Cars2+/− mice were normally born without any apparent abnormalities in macroscopic appearance or growth profiles during the observa-tion period of at least 6 months after birth, but they demonstrated reduced mitochondrial expression of CARS2 protein by half and marked attenuation of CysSSH production; in contrast, we observed no appreciable change in mitochondrial DNA-encoded MTCO1, which indicated intact Cys-tRNA synthetase activity in Cars2+/− mice (FIG. 5c-e). About the features discussed here, a paper, "M. IKEDA et al, Distribution of Polysulfide in Human Biological Fluids and Their Association with Amylase and Sperm Activities, Molecules, vol. 24,1689, 2019," is incorporated by reference. Therefore, we quantified the sulfide metabolites in the liver of Cars2+/− mice and their WT littermates via LC-MS/MS analysis with HPE-IAM as described earlier. As we expected, CARS2+/− mice showed a striking difference in persulfide production compared with the WT littermates (FIG. 6a, b). Endogenous levels of CysSSH and all other derivatives (e.g., GSSH, HS—, thiosulfate, and hydropolysulfides) decreased by 50% or more in the liver and lung of Cars2+/− mouse compared with WT mice.

To exclude the possibility of off-target effects by the gRNA used to produce line 1 Cars2+/− mice, we developed another strain of Cars2+/− mice (line 2) with an alternative gRNA targeting Cars2 exon 3. Line 2 Cars2+/− mice had phenotypes almost identical to those of line 1. About the feature(s) in the paragraph, two papers, "1) T. ZHANG et al, Enhanced Cellular Polysulfides Negatively Regulate TLR4 Signaling and Mitigate Lethal Endotoxin Shock, Cell Chemical Biology, 26, 686-698, May 16, 2019" and "2) T. TAKATA, The active-site cysteine residue of Ca2+/calmodulin-dependent protein kinase I is protected from irreversible modification via generation of polysulfidation, Nitric Oxide, 86, P68-75, 2019," are incorporated by reference.

That heterozygous Cars2 mutant mice manifested a CysSSH reduction by ~50% should be noted; it suggests that Cars2 contributes almost entirely to the CysSSH production in mouse tissues under physiological conditions. As an important finding, Cars2 disruption did not alter expression levels of other sulfide-metabolizing enzymes, including CSE, CBS, and 3-mercaptopyruvate sulfur transferase (3-MST) (FIG. 5e), which emphasized the sole contribution of CARS2 to endogenous persulfide biosynthesis in vivo. About the feature(s) in the paragraph, two papers, "1) M. IKEDA et al, Distribution of Polysulfide in Human Biological Fluids and Their Association with Amylase and Sperm Activities, Molecules, vol. 24,1689, 2019" and "2) T. TAKATA, The active-site cysteine residue of Ca2+/calmodulin-dependent protein kinase I is protected from irreversible modification via generation of polysulfidation, Nitric Oxide, 86, P68-75, 2019," are incorporated by reference.

Figure 7:
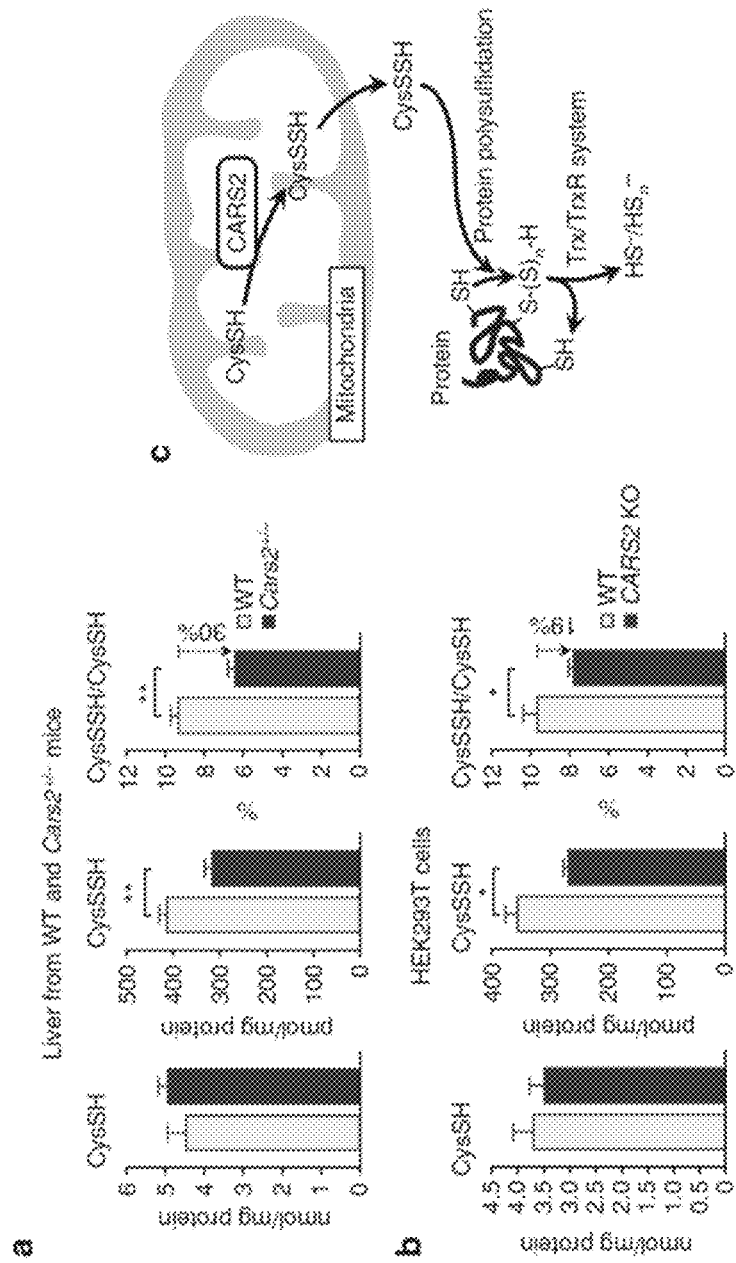
FIG. 7 shows endogenous protein polysulfidation in vivo and in HEK293T cells.

To explore the possibility that CARS2, a mitochondrial protein, can produce CysSSH and provide it to the whole cell, we isolated mitochondria from mouse liver and measured the release of de novo-synthesized CysSSH from the mitochondria. About the feature, a paper, "Y. KISHIMOTO et al, 8-Nitro-cGMP attenuates context-dependent fear memory in mice, Biochemical and Biophysical Research Communications (BBRC), 511, p 141-147, 2019," is incorporated by reference. A large fraction of CysSSH was indeed released from mitochondria, which supports the idea that CysSSH produced in mitochondria is released into the cytoplasm and maintains protein polysulfidation. As expected, CysSSH derived from whole-cell proteins was decreased in Cars2+/− mice, but cysteine (CysSH) did not (FIG. 7). Specifically, formation of 20-30% of CysSSH in all cell proteins (polysulfidation) depended on CARS2 expression not only in the in vivo experiment using Cars2 KO mice (FIG. 7a) but also in the in vitro cell culture study (FIG. 7b), as identified by HPE-IAM labeling LC-MS/MS analysis with the whole cell and tissues proteins isolated. These results suggest that CysSSH derived from CARS2 significantly contributes to the polysulfidation of the whole-cell proteins. Because protein polysulfidation appears to be mediated via post-translational as well as co-translational processes, the former being controlled by the thioredoxin (Trx)—Trx reductase (TrxR) system as recently reported4, we expect that CysSSH generated in mitochondria is released into the cytoplasm and supplies sulfur to proteins for polysulfidation (FIG. 7c). Our current evidence is the first demonstration that unequivocally verified in human cultured cells and in vivo in mice that CARS2 is the major enzyme for persulfide biosynthesis and thus functions as a CPERS in mammals.

CARS-mediated polysulfidation and mitochondrial physiology. Unexpectedly, CARS2 KO cells showed markedly altered mito-chondrial morphology (i.e., shrunken or fragmented appearance), which greatly improved when CARS2 was added back, as seen with the MitoTracker Red fluorescent mitochondrial stain (FIG. 8a), transmission electron microscopy (FIG. 8b), and immunofluorescence staining for translocase of outer mitochondrial membrane 20 (TOMM20) and CARS2. Not only WT CARS2 but also the C78/257D mutant induced a strikingly improved mitochondrial morphology, but other Lys mutants tested did not (FIG. 8a, b). In line with these findings, deletion of CARS2 activated dynamin-related protein (Drpl), a major med-iator of mitochondrial fission33, and Drpl GTPase activity was significantly attenuated by adding back the WT CARS2 and C78/257D mutant, thereby producing CysSSH without CARS activity, but not by adding back the K317/320A mutant (FIG. 8c). Usually, Drpl in HEK293T cells was extensively polysulfidated (FIG. 8d), as evidenced by our new biotin-PEG-MAL capture method (Supplementary FIG. 3b). However, Drpl polysulfidation was markedly suppressed by both CARS2 KO and additional CARS1/2 double-knockdown, respectively (FIG. 8d). Because Drpl is likely activated via chemical depoly-sulfidation or a post-translational process operated physiologi-cally by the Trx-TrxR system, for example, we identified Drpl as a major signal effector molecule reversibly regulated through a unique polysulfidation and depolysulfidation process (FIG. 8e). About the features discussed in the paragraph, two papers, "1) M. AKIYAMA et al, Erratum: Environmental Electrophile-Mediated Toxicity in Mice Lacking Nrf2, CSE, or Both, Environmental Health Perspectives, Vol. 127 (6) June 2019," and "2) J. LIN et al, The Uptake and Release of Polysulfur Cysteine Species by Cells: Physiological and Toxicological Implications, Chemical Research in Toxicology, 32, p 447-455, 2019," are incorporated by reference.

We next examined CARS2 contribution to mitochondrial biogenesis and function. Mitochondrial DNA normalized against nuclear DNA was reduced in CARS2 KO cells, which was similarly restored by WT CARS2 and C78/257D but not by Lys mutants (Supplementary FIG. 24a), which suggests that CARS2-derived persulfide enhances mito-chondrial biogenesis. Mitochon-drial membrane potential was decreased in CARS2 KO cells, but it recovered or even increased when the WT and C78/257D mutant were added back or overexpressed but not when Lys mutants were used (FIG. 8f). We also used an extracellular flux analyzer to measure the oxygen consumption rate (OCR) in HEK293T CARS2 KO cells. The OCR in CARS2 KO cells was ~50% of that in WT cells (FIG. 8g), consistent with the incomplete elimination of CARS2 protein and thereby attenuated expression of MTCO1 in CARS2 KO cells (FIG. 4g). The decrease of OCR in CARS2 KO cells was recovered by introduction of WT CARS2 and C78/257D mutant but not by Lys mutants (FIG. 8g). A novel concept emerging from these observations is that CARS2-derived cysteine persulfides play an important role in the electron transport chain (ETC) in mitochondria, which sheds light on a completely new and fundamental role of persulfides in supporting mitochondrial bioenergetic function. About the features discussed in the paragraph and paragraph [0035], two papers, "1) S. FUJII, Persulfide synthases that are functionally coupled with translation mediate sulfur respiration in mammalian cells, British Journal of Pharmacology, 176, p 607-615, 2019" and "2) C. Bianco, The reaction of hydrogen sulfide with disulfides: formation of a stable trisulfide and implications for biological systems, British Journal of Pharmacology, 176, p 671-683, 2019," are incorporated by reference.

CARS2 linked up to mitochondrial ETC. In our efforts to elu-cidate the mechanism of how CARS2-derived CysSSH contributes to the mitochondrial bioenergetics function, we noticed a quite different profile of the products of human CARS2 in the cell-free enzyme reaction compared with cellular CARS2 metabolism in HEK293T cells in culture (FIG. 9a, b). Although CARS2 synthe-sized mostly CysSSH/SSSH in a cell-free solution (FIG. 3c, d), preferential formation of HS— (H2S) together with thiosulfate (SO32-) over CysSSH was evident with HEK293T cells. We thus hypothesized that the mitochondrial compartment is a unique metabolic environment in which de novo CysSSH synthesized by CARS2 may be further metabolized, possibly being coupled with the mitochondrial ETC.

To understand how the ETC function and CysSSH derived from CARS2 are associated (FIG. 8g), we examined the effect of ETC suppression on the metabolic profile of CysSSH and its derivatives in HEK293T cells (FIG. 9c-h). About the feature here, the paper "C. Bianco, The reaction of hydrogen sulfide with disulfides: formation of a stable trisulfide and implications for biological systems, British Journal of Pharmacology, 176, p 671-683, 2019," is incorporated by reference. We then used two approaches to inhibit the ETC in the cells: one method was to use a specific inhibitor of complex III, antimycin A (FIG. 9c-e), and the other ETC disrupter used was ethidium bromide to induce mitochondrial DNA deprivation (FIG. 9f-h). About the method, the paper "S. FUJII, Persulfide synthases that are functionally coupled with translation mediate sulfur respiration in mammalian cells, British Journal of Pharmacology, 176, p 607-615, 2019" is incorporated by reference. Both ETC suppressive treatments caused a significant increase in CysSSH and simultaneous reduction of HS-production, as assessed by the HPE-IAM labeling LC-MS/MS analysis (FIG. 9c-h). These inverse and stoichiometric relation-ships between CysSSH and hydrosulfide anion (HS—) formation strongly suggested an ETC activity-dependent conversion of CysSSH to HS— mediated via the ETC occurring in the cells (FIG. 9e, h). We interpret these results to mean that CysSSH derived from CARS2 in mitochondria is effectively reduced by accepting an electron from the ETC to release HS— (H2S), as FIG. 9i illustrates.

These data thus provide robust support for the idea that the CARS2-CysSSH pathway is involved in the mitochon-drial function because CARS2-dependent CysSSH production is functionally integrated into and tightly linked to the mitochon-drial ETC, which is in turn involved in the energy metabolism, as FIGS. 10A and 10B illustrate. In fact, low (nM) concentrations of H2S reportedly sustained the ETC function possibly mediated by sulfide:quinone reductase and other potential enzymes that oxidize sulfides to thiosulfate (SO32-)7,34-38. How H2S is supplied endogenously in mitochondria remained unclear, however. Our earlier and current studies suggest that CSE, CBS, and 3-MST are not major sources of H2S in mitochondria in various mammalian cell lines and in mice in vivo (FIG. 5e)7,20-24. In this context, our study is the first to verify that HS— (or H2S) is indirectly formed from CARS2 via CysSSH generation in the mitochondrial environment (FIGS. 9i and 10). Moreover, our recent study determined that CysSSH contributed to the endogenous formation of iron-sulfur clus-ters14. Because iron-sulfur clusters are known to be synthesized and utilized in complexes I-III of the ETC in mitochondria39, and are actively transported extramitochondrially, the CysSSH-dependent HS-metabolism may be coupled with the generation of iron-sulfur centers of the mitochondrial ETC and cytosolic formation and maintenance of various iron-sulfur complex machineries as well. Our reasonable conclusion is, therefore, that CARS2 functions as a major CPERS, which in turn promotes mitochondrial biogenesis and bioenergetics (FIGS. 10A and 10B).

DISCUSSION

Until now, endogenous persulfides were thought to be formed as a result of H2S/HS-oxidation via post-translational processes, and serve as protein cysteine thiol-bound intermediates of detoxification enzymes3,7,21, and as metal ligands for iron and zinc complexes11-15. While CSE and CBS can catalyze CysSSH biosynthesis by using cystine as a substrate3,4,6-10,18-21, several cells and tissues without CSE/CBS expression and CBS/CSE KO mice reportedly synthesized appreciable amounts of persulfides3,20,22-24, but the source of the persulfides (polysulfides) or the sulfane sulfur reservoir has remained elusive. We here demonstrate that CARSs catalyze CysS-(S)n-H formation from cysteine and co-translational protein polysulfidation. Also, CSE and CBS may still play a major role in the CysSSH pro-duction via the direct catalytic reaction using cystine as the substrate especially under pathophysiological conditions associated with oxidative and electrophilic stress, where intracellular cystine concentrations are considerably approaching the high Km value of CSE3,7,21,40-42.

The second, even more crucial, finding is that the mitochon-drion is a key cellular compartment for the formation and action of CysSSH and CysS-(S)n-H. Notably, CysSSH is mostly generated by CARS2 localized in the mitochondria and is released extramitochondrially into the cytoplasm so that it can effectively produce CysS-(S)n-H and protein polysulfidation in whole-cell compartments. The current study established that CARS2-derived CysSSH (CysS-(S)n-H) indeed sustains mitochondrial biogenesis and the ETC function. While the implications of these findings await further investigation, a recent clinical study by Coughlin et al. documented an intriguing result: CARS2 mutations identified in a patient were associated with ETC impairment and mitochondrial dysfunctions31. Although the patient's clinical symptoms resulted from loss of a canonical function of CARS2, which the neurological disorders might be caused by impairment of CPERS activity of CARS2 is plausible, and thus this impaired activity may overlap with the observed impairment of Cys-tRNA aminoacylation.

The nature of sulfane sulfur or polysulfides has continued to be a puzzle for a long time, because of a complicated polysulfide chemistry with dual electrophilic and nucleophilic characteristics. Previous reports demonstrated the ability of a trisulfide species to react with numerous electrophiles. For example, Fletcher and Robson reported that thiocystine (cystine trisulfide, CysSSSCys) readily reacted with electrophilic halogens (e.g., Br2), which resulted in cleavage of the S—S bond25. A review by Parker and Kharasch also discussed numerous examples of the electrophilic cleavage of the S—S bond in disulfides by electrophilic reagents such as protons, sulfenium ions, and halogens26. More recently (and directly relevant to our studies), Abdolrasulnia and Wood reported that CysSSSCys reacted readily with iodoacetic acid (a well-established thiol-modifying agent) to ultimately give car-boxymethylthiocysteine (CysSS-CH2COOH)27, which is con-sistent with the idea that a nucleophilic sulfur atom of the polysulfide reacted with the electrophilic iodoacetic acid species and led to S—S bond cleavage. Previous examination of the reaction of electrophiles with disulfides (the simplest of all polysulfides) is entirely consistent with this idea28. Thus, ample precedence for the nucleophilic character of polysulfides exists, by capitalizing on such a unique property, we are now able to identify the cysteine and protein polysulfidation occurring endogenously by means of a conventional PMSA or capturing assays and even by using HPE-IAM labeling LC-MS/MS analysis. The present discovery of a novel polysulfide biosynthesis, there-fore, can now explain substantial endogenous generation of sul-fane sulfur, which we clarified as composed of various polysulfide derivatives and which is biosynthesized by CPERSs and CARSs.

Our findings raise a number of important questions; however, for example, why are such protein-bound cysteines abundantly polysulfidated, does polysulfidation affect protein folding? And, what function does this modification play in compartments other than mitochondria?Determining how CPERS activity is regulated will also be important. Given the powerful effects of persulfides on mitochondrial morphology and bioenergetics, the availability of persulfides in cells must be subject to stringent regulation. Although CPERSs play a critical role in generating CysSSH, the Trx-TrxR system may help maintain cellular persulfide con-centrations within certain limits by controlling the rate of per-sulfide degradation4.

Some aminoacyl-tRNA synthetases reportedly possess func-tions in physiological processes besides their role in translation43. The mitochondria-promoting functions of CARS2 suggest its non-canonical roles and therefore may therefore represent "moonlighting" roles of CARS2. However, CARSs effectively synthesize cysteine polysulfides, and this process is closely related to the initial translational process of de novo synthesis of nascent polypeptides in ribosomes (cf. FIG. 1b and FIGS. 10A and 10B). The CPERS function of CARSs is apparently associated not only with translation but also with the mitochondrial respiration, which indicates that CARSs, rather than having a moon-lighting role, have a primary function of producing persulfides.

In conclusion, our discovery of reactive persulfide production mediated by the CARS or CPERS pathway and the potent effects on mitochondrial functions observed would seem to represent a significant evolution of molecular and cell biology, thereby inviting a paradigm shift in the current understanding of cellular translation, redox signaling, and energy metabolism (FIGS. 10A and 10B). Our discovery of CARS and CPERS as a major sources of reactive persulfides in biology may usher in a new era of modern redox biology and life science research that hold great potential to invigorate translational studies in a variety of disease processes known to be associated with aberrant redox regulation and mitochondrial dysfunction.

Methods

LC-ESI-MS/MS analyses for per/polysulfides. LC-ESI-MS/MS analysis with HPE-IAM (Supplementary FIG. 5 and Supplementary Table 2) was used to determine CysSSH or CysS-(S)n-SH formed from EcCARS and CARSs. To identify CysS-(S)n-H formed and incorporated into Cys-tRNA via the enzymatic reaction of EcCARS, 200 μg/ml recombinant EcCARS was reacted with 0.5 mg/ml tRNA (Sigma- Aldrich) and CysS-(S)n-H or 10 μM cysteine as the substrate, in 50 mM HEPES buffer (pH 7.5) containing 1 mM ATP, 25 mM KCl, and 15 mM MgCl2 at 37° C., followed by alkylation with 1 mM HPE-IAM for 20 min at 37° C. CysS—(S)n-H were formed from 10 μM cystine and 30 μM Na2S2 in 30 mM HEPES buffer pH 7.5 at 37° C. for 5 min. The Cys-tRNACys-(S)n-H synthesized by EcCARS was precipitated by adding 10% trichloroacetic acid to the reaction mixture, followed by trapping by cotton wool filters (100 μl) placed in pipette tips. The precipitated total tRNA containing Cys-tRNACys-(S)n-H was washed with 10% trichloroacetic acid (200 μl twice) and with 70% ethanol (200 μl twice) to completely remove the free cysteine and CysS-(S)n-H. CysS-HPE-IAM and CysS-(S)n-HPE-IAM adducts were dissociated by alkaline heat hydrolysis of the ester bond of aminoacyl moieties of the Cys-tRNACys and Cys-tRNACys-(S)n-H. The hydrolysis was performed in 20 mM Tris-HCl (pH 8.0), which contained known amounts of stable isotope-labeled internal standards, at 70° C. for 15 min. The eluted solutions were acidified with formic acid and analyzed via LC-ESI-MS/MS. Also, Cys-tRNA-bound CysSSH was identified by detecting a CysSSH-adenosine adduct formed in the Cys-tRNA molecules synthesized by EcCARS from the substrate cysteine. The CysSSH-adenosine adducts in the reaction of EcCARS with cysteine and Cys-tRNA were measured by using LC-ESI-MS/MS analysis. In brief, CysSSH incorporated into tRNA as catalyzed via EcCARS with cysteine was prepared in the same manner as that described above, followed by alkylation with HPE-IAM and acetylation with acetic anhydride, as described earlier44. After precipitation and washing of samples with ethanol, the acetylated and HPE-IAM-labeled CystRNA-CysSSH was digested to generate acetylated CysSS-HPE-AM-bound adenosine by treatment with RNase ONE (Promega, Madison, WI) at 37° C. for 1 h, after which LC-ESI-MS/MS ana-lysis was performed. To measure CysS-(S)n-H generated directly by EcCARS and CARSs, recombinant EcCARS, mouse CARS1, or human CARS2 was incubated with cysteine in 50 mM HEPES buffer (pH 7.5) containing 25 mM KCl and 15 mM MgCl2 with or without 1 mM ATP at 37° C. The mixtures were then reacted with 1 mM HPE-IAM in methanol at 37° C. for 20 min to form CysS-(S)n-HPE-IAM adducts. After centrifugation, aliquots of the supernatants were diluted 10-100 times with 0.1% formic acid containing known amounts of isotope-labeled internal standards and were subjected to LC-ESI-MS/MS. To clarify the molecular mechanism of CysSSH formation, 50 μM 34S-labeled L-cysteine was reacted with 200 μg/ml EcCARS as a substrate in 50 mM HEPES buffer (pH 7.5) containing 25 mM KCl and 15 mM MgCl2 at 37° C. for 15-60 min. The reaction products treated with HPE-IAM were diluted with 0.1% formic acid containing known amounts of isotope-labeled internal standards, which were then subjected to LC-ESI-MS/MS as described above. To determine kinetic parameters, WT EcCARS and C28S EcCARS were incubated with different concentrations of L-cysteine in 50 mM HEPES buffer (pH 7.5) containing 25 mM KCl and 15 mM MgCl2 at 37° C. for 30 s. The reaction mixtures were treated with 1 mM HPE-IAM, followed by LC-ESI-MS/MS as described above. The data were fitted by nonlinear regression to the Michaelis-Menten equation by using GraphPad Prism software ver. 6.0 (GraphPad Software, San Diego, CA) to obtain the kinetic parameters. Each calculated enzyme parameter was compared with that of recombinant CSEs (rat and human), which we obtained from the enzymatic reaction with L-cystine as the substrate, according to our previous report3. For analysis of intracellular persulfide levels in cultured HEK293T cells, and livers and lungs obtained from WT and Cars2+/− littermate mice, the cultured cells and mouse tissues were lysed or homogenized in a cold methanol solution containing 1 mM HPE-IAM, after which cell lysates were incubated at 37° C. for 20 min. After centrifugation, aliquots of the supernatants of the lysates were diluted 20 times with 0.10% formic acid containing known amounts of isotope-labeled internal standards, which were then analyzed via LC-ESI-MS/MS for per/polysulfide determination. A triple quadrupole (Q) mass spectrometer LCMS-8050 (Shimadzu) coupled to the Nexera UHPLC system (Shimadzu) was used to perform LC-ESI-MS/MS. Per/polysulfide derivatives were separated by means of Nexera UHPLC with a YMC-Triart C18 column (50×2.0 mm inner diameter) under the following elution conditions: mobile phases A (0.1% formic acid) with a linear gradient of mobile phases B (0.1% formic acid in methanol) from 5 to 90% for 15 min at a flow rate of 0.2 ml/min at 40° C. MS spectra were obtained with each temperature of the ESI probe, desolvation line, and heat block at 300, 250, and 400° C., respectively; and the nebulizer, heating, and drying nitrogen gas flows were set to 3, 10, and 10 liters/min, respectively. Various per/polysulfide derivatives were identified and quantified by means of multiple reaction monitoring (MRM). Supplementary Table 2 summarizes the MRM parameters for each derivative.

Identification of CysS-(S)n-SH formed in nascent peptides. CysS-(S)n-SH species synthesized endogenously and formed in nascent polypeptides by EcCARS in E. coli cells in culture were analyzed by means of puromycin-associated nascent chain proteomics (PUNCH-P)29, which was specifically modified here for polysulfidated proteins (PUNCH for Polysulfide Proteomics, henceforth called PUNCH-PsP). The E. coli JM109 cells transfected with an hGAPDH expression vector (pGE-30) were cultured and hGAPDH expression was induced with IPTG as described earlier, followed by collecting and sonication of the cells in cell lysis buffer containing 0.3 mg/ml lysozyme and 2 mM IAM without any reducing agents. The supernatant obtained by centrifugation was applied to the Ni-NTA agarose column for purification of the mature GAPDH protein. From the resultantpellet of the E. coli cell lysate, the ribosomal fraction was isolated via sucrose density gradient ultracentrifugation, as reported previously29. The ribosomal fraction was suspended in polysome buffer (50 mM Tris-HCl, pH 7.5, 10 mM MgCl2, and 25 mM KCl), containing an EDTA-free protease inhibitor cocktail (as indicated by the manufacturer), and was then reacted with 2 mM IAM at room temperature for 30 min. After the ribosomal fraction was washed with the poly-some buffer, the ribosomes were treated with 5'-biotin-dC-puromycin (Jena Bioscience, Jena, Germany) in TTBS (20 mM Tris-HCl, 150 mM NaCl, 0.1% Tween 20, pH 7.6) at 37° C. for 15 min and were then reacted with avidin magnetic beads (Wako Pure Chemical Industries) to finally capture the newly synthesized polypeptides in ribosomes in the E. coli cells in culture. The puromycin-labeling con-ditions were optimized for the E. coli ribosomes used in the present study, according to the original report29. The CysS-(S)n-H residues in GAPDH were detected by means of LC-Q-TOF-MS as described earlier, with tryptic digests of the mature GAPDH purified simultaneously and the same digest of the nascent GAPDH polypeptides within the cultured E. coli ribosomes captured with and recovered from the biotin-puromycin-bound avidin beads. CysS-(S)n-H in the nascent polypeptides can be selectively identified by using PUNCH-PsP, which we successfully developed and describe here (FIG. 1c and FIGS.

10A and 10B). During this PUNCH-PsP analysis, the cysteine and CysS-(S)n-H residues located in the polysulfide exit tunnel in the ribosomes are not accessible to exogenously added IAM and can thus be protected from alkylation by IAM because of the unique physicochemical properties of the interior structure of the polypeptide exit tunnel in the ribosome45-47, which allowed us to obtain specific and selective identification of the intact forms of CysS-(S)n-H residues in the nascent peptides present only within the ribosomes, as FIG. 10A shows. As soon as the mature GAPDH isolated from $E.$ $coli.$ with the Ni-NTA agarose was treated by quick digestion with 10 μg/ml trypsin at 37° C. for 30 min, which was promptly subjected to the LC-ESI-Q-TOF analysis, in a similar manner as shown for the PUNCH-PsP method.

Preparation and purification of recombinant CARS proteins. To generate recombinant CARSs, open-reading frames of these genes were transferred into AG1 (Agilent Technologies, Santa Clara, CA) competent cells. Recombinant EcCARS, mouse CARS1, and human CARS2 proteins were purified by using the following standard procedure. Briefly, these proteins were produced in AG1, and they were purified by using nickel nitrilotriacetic acid agarose; resultant purified proteins were extensively dialyzed against phosphate buffer and stored at −80° C. until use. Protein concentration was determined by using the Protein Assay CBB Solution (Nacalai Tesque, Kyoto, Japan), and protein purity was confirmed via SDS-PAGE.

Generation of CARS2 KO cell lines. The genome editing CRISPR/Cas9 system was used to generate human CARS2 KO cell lines. To obtain gRNA, which is highly specific for the first exon of the human CARS2 locus and has fewer off-target sites within the human genome, we based an optimal gRNA design on the software program CRISPRdirect48. To express Cas9 and gRNA in HEK293T cells, the pX459 V2.0-CARS2 gRNA vector was created by inserting annealed oligonucleotide pairs (5'-caccTGGGCCTTGGGCGGGCTGGG-3' (SEQ ID NO:13) and 5'-aaacCCC AGCCCGCC-CAAGGCCCA-3' (SEQ ID NO:14)) into the BpiI sites of pX459 V2.0. pX459 V2.0 vector, which enables expression of a gRNA (directed to the CARS2 exon 1), SpCas9, and a puromycin resistance gene from a single vector, was obtained from the Zhang laboratory via Addgene plasmid 6298849. About the feature, the paper, "C. Bianco, The reaction of hydrogen sulfide with disulfides: formation of a stable trisulfide and implications for biological systems, British Journal of Pharmacology, 176, p 671-683, 2019," is incorporated by reference. HEK293T cells were plated in 6-well plates (1.0×105 cells per well) 24 h before transfection. Cultured cells were transfected with 2 μg of pX459 V2.0-CARS2 gRNA by using Lipofectamine 2000 (Invitrogen, Carlsbad, CA). The medium was changed 24 h after transfection. After another 24 h of incubation, the cells were replated on 10-cm dishes and cultured for various time periods at 37° C. with a selection medium containing 2.0 μg/ml puromycin (Invitrogen). Puromycin-resistant clones were arbitrarily selected and used for screening CARS2 KO cell lines to finally obtain stable CARS2 KO cell lines. Disruption of the CARS2 gene was verified by loss of CARS2 protein expression as determined by western blotting.

Construction of mammalian hCARS2 expression vectors. To produce an hCARS2 expression vector (pPyCAGIP-FLAG-hCARS2), the XhoI fragment of pET-15b-hCARS2 was cloned into the XhoI site of pPyCAGIP-FLAG. The same vectors containing various mutant hCARS2 genes were obtained via site-directed mutagenesis by using inverse PCR with pPyCAGIP-FLAG-hCARS2 as a template and primer sets for generation of pPyCAGIP-FLAG-hCARS2 C78/257D, K124/127A, and K317/320A.

Transfection of various CARS2 genes and knockdown of CARS1/2. WT and various mutant CARS2 genes were transfected into HEK293T WT and mutant cells as reported recently3 by using expression plasmids such as pPyCAGIP-FLAG-hCARS2 and CARS2 mutant vectors.

Transfection of the expression plasmid was performed by using Lipofectamine 2000 according to the manufacturer's instructions. In brief, we incubated WT and CARS2 KO HEK293T cells seeded in 24-well plates (6×105 cells per well) and 8-well culture slides (2×105 cells per well) for 12 h at 37° C. For transfection, we mixed 1.5 μg per well of the expression plasmid with 50 μl of Opti-MEM (Invitrogen) in a tube. Before plasmid DNA and transfection reagent solutions were added to the cells, solutions were mixed together and incubated for 5 min at room temperature and then added to the cells, after which incubation proceeded for 30 h or 3 days. Also, knockdown of CARS1 and CARS2 was performed as reported recently3 by using the following small interfering RNAs (siRNAs): CARS1, CARSHSS101368 (Invitrogen), and CARS2, CARS2HSS128464 (Invitrogen). siRNA transfection was performed by using Lipofectamine RNAiMAX (Invitrogen) according to the manufacturer's instructions. The siRNA was introduced into WT and CARS2 KO cells, as described above for CARS2 gene transfection.

Figure 6:
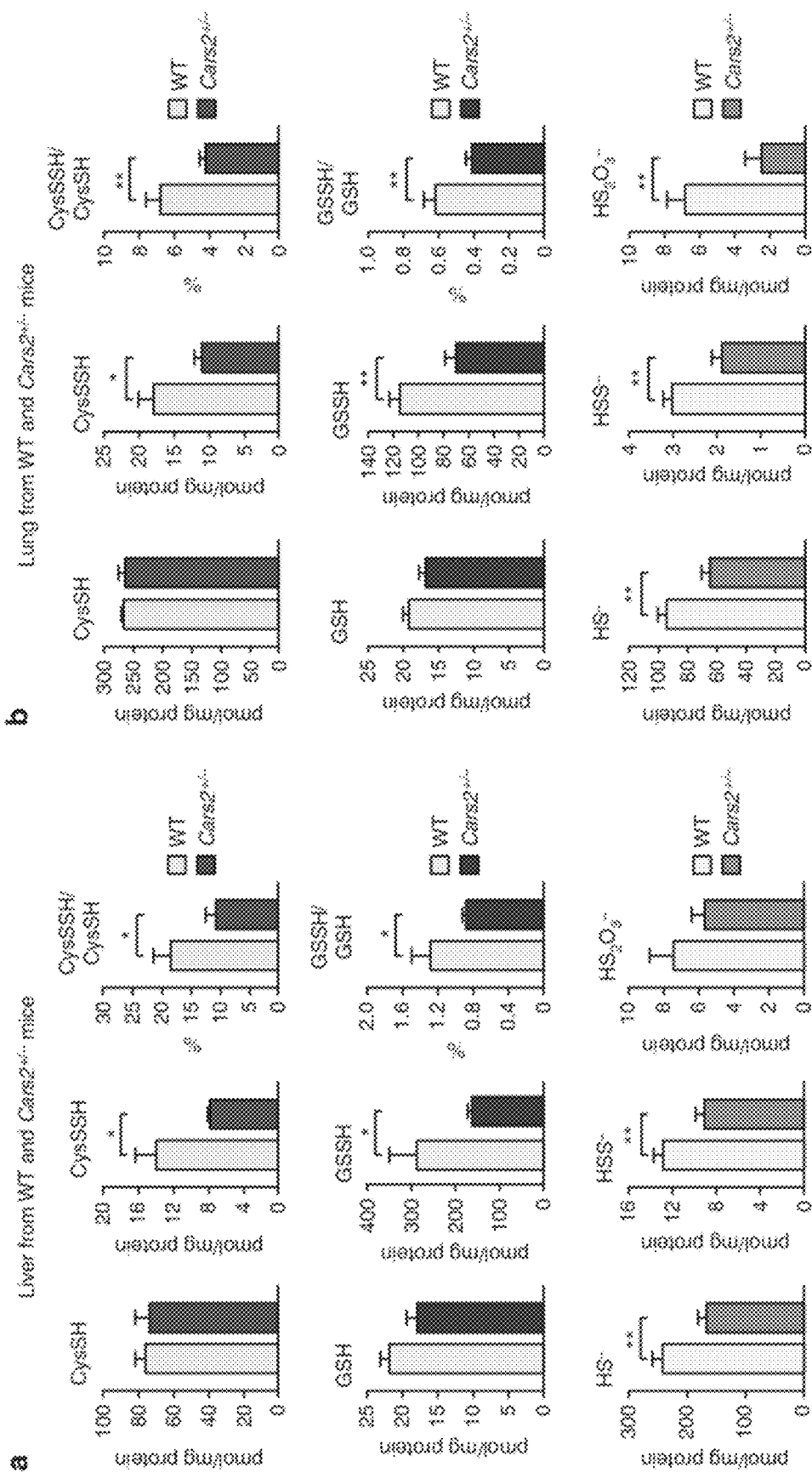
FIG. 6 shows in vivo formation of various sulfide species in WT and Cars2$^{+/-}$ mice.

Generation of Cars2-deficient mice. All experimental procedures conformed to "Regulations for Animal Experiments And Related Activities at Tohoku Uni-versity", and were reviewed by the Institutional Laboratory Animal Care and Use Committee of Tohoku University, and finally approved by the President of Uni-versity. We generated two lines of Cars2-deficient mice as follows. Cars2 gRNAs vectors were constructed with use of a pT7-sgRNA and pT7-hCas9 plasmid (a gift from Dr. M. Ikawa, Osaka University)50. After digestion of pT7-hCas9 plasmid with EcoRI, hCas9 mRNA was synthesized by using an in vitro RNA transcription kit (mMESSAGE mMACHINE T7 Ultra kit; Ambion, Austin, TX), according to the manufacturer's instructions. A pair of oligonucleotides targeting Cars2 was annealed and inserted into the BbsI site of the pT7-sgRNA vector. The sequences of the gRNAs were designed as follows: 5'-GGACAGATCCAGCGAACAGG-3' (SEQ ID NO:15) and 5'-AATAATCAAGAGAGCTAACG-3', (SEQ ID NO:16) located at exons 1 and 3 of Cars2 gene, to generate CARS2-deficient lines 1 and 2 mice, respectively. After digestion of pT7-sgRNA with XbaI, gRNAs were synthesized by using the MEGAshortscript kit (Ambion). We used C57BL/6N female mice (purchased from Crea-Japan Inc., Tokyo, Japan) to obtain C57BL/6N eggs, and we performed in vitro fertilization with these eggs. In brief, Cas9 mRNA and gRNA were introduced into fertilized eggs by injecting using a Leica Micromanipulator System, according to the pro-tocols reported previously50, after which we transferred the eggs to the oviducts of pseudo-pregnant females on the day of the vaginal plug. A founder mouse har-boring the Cars2 mutant alleles was crossed with WT mice to obtain Cars2 het-erozygous mice. After segregating the Cars2 mutant alleles, heterozygous mice with a 200-bp deletion in exon 1 (line 1) and with a 1-bp insertion in exon 3 were selected for additional analyses (FIGS. 5-7). About the features discussed in the paragraph, the papers, "T. ZHANG et al, Enhanced Cellular Polysulfides Negatively Regulate TLR4 Signaling and Mitigate Lethal Endotoxin Shock, Cell Chemical Biology, 26, 686-698, May 16, 2019" and "T. TAKATA, The active-site cysteine residue of Ca2+/calmodulin-dependent protein kinase I is protected from irreversible modification via generation of polysulfidation, Nitric Oxide, 86, P68-75, 2019," are incorporated by reference.

MitoTracker Red staining for mitochondrial morphology. To analyze mito-chondrial morphogenesis under several experimental conditions in cells, mito-chondria were imaged by using the fluorescent probe MitoTracker Red CM-H2Xros (Invitrogen). In brief, culture slides were coated with 0.5% polyethylene imine for more than 1 h and washed twice with PBS. CARS2 KO cells were transfected with expression plasmids for WT and individual mutants of human CARS2 via Lipofectamine 2000. At 3 days after transfection, cultured cells were washed with Hank's buffer, incubated with 1 μM MitoTracker Red CM-H2Xros at 37° C. for 30 min, rinsed twice with Hank's buffer, and examined with a Nikon EZ-C1 confocal laser microscope (Tokyo, Japan). We used ImageJ and Prism software for image processing and quantification of mitochondrial dimensions including their length.

Mitochondrial bioenergetic functions. To determine the membrane potential (ΔPm) of mitochondria under several experimental conditions, tetra-ethylbenzimidazolyl carbocyanine iodide (JC-1) staining was performed according to the manufacturer's protocol. Accumulation of the cell-permeable JC-1 probe (Abcam) in mitochondria depends on the membrane potential, associated with a fluorescence emission shift from green to red. Briefly, WT and CARS2 KO HEK293T cells, cultured in 8-well multichamber Millicell slides coated with PEI, were treated with various CARS2 vectors or were untreated, as described above. For JC-1 staining, cultured cells were washed with HKRB buffer (20 mM HEPES, 103 mM NaCl, 4.77 mM KCl, 0.5 mM CaCl2), 1.2 mM MgCl2, 1.2 mM KH2PO4, 25 mM NaHCO$_3$ and 15 mM glucose, pH 7.3), incubated with 20 μM JC-1 at 37° C. for 30 min, rinsed twice with HKRB buffer, and examined with a Nikon EZ-C1 confocal laser microscope. ImageJ software was used for image processing and quantification of the JC-1 fluorescent responses.

Mitochondrial bioenergetic functions. Mitochondrial function was investigated, according to a previous report with a slight modification51, by measuring the basal OCR of the mitochondria under various experimental conditions in WT and CARS2 KO cells, using the XF96 Extracellular Flux Analyzer (Seahorse Bioscience, Agilent). At the end of the experiment, rotenone and antimycin A (2.4 μM each) were added to inhibit complexes I and III of the mitochondrial electron transport chain, respectively, to determine the remaining mitochondria-independent OCR. Net OCR was normalized to the cell number determined at the end of the experiments by means of sulforhodamine B staining (Sigma-Aldrich, St. Louis, MO). To obtain the mitochondria-specific OCR, only the rotenone/antimycin-sensitive part of cell respiration was used.

Effect of suppression of ETC on metabolic profiles of CysSSH. The mito-chondrial ETC in HEK293T cells was inhibited either by a complex III inhibitor, antimycin A, or by elimination of mitochondrial DNA (mtDNA) induced by ethidium bromide. For the direct but partial ETC (complex III) inhibition, WT and CARS2 KO cells were treated with various concentrations of antimycin A for 1 h, followed by methanol extraction for measurement of CysSSH and its related sulfide derivatives by HPE-IAM labeling LC-ESI-MS/MS analysis as described earlier. To indirectly suppress all ETC components (complexes), mtDNA from WT and CARS2 KO HEK293T cells was eliminated specifically by treatment with ethidium bromide (50 ng/ml, 127 nM) for 12 days under standard cell culture conditions (37° C., humidified, 5% CO2/95% air) with DMEM containing 10% FBS, 1% penicillin-streptomycin, sodium pyruvate (1 mM), non-essential amino acids (1%), and uridine (50 μg/ml), according to a previous method with a slight modifica-tion52. The cells without mtDNA were then subjected to HPE-IAM labeling LC-MS/MS analysis for persulfide metabolic profiling, similar to antimycin-treated cells. The efficacy of the present mtDNA elimination and the resultant ETC suppression were assessed by measuring mtDNA as described below, and these results were confirmed by substantial suppression of mito-chondrial cytochrome c oxidase subunit 1 (MTCO1: encoded by mtDNA), as identified by western blotting. About the feature here, a paper, "S. FUJII, Persulfide synthases that are functionally coupled with translation mediate sulfur respiration in mammalian cells, British Journal of Pharmacology, 176, p 607-615, 2019," is incorporated by reference. In contrast, MitoTracker Red staining showed no appreciable altered morphology of mitochondria in HEK293T cells with or without ethidium bromide treatment, at least under the present experimental conditions. The quantity of each sulfide produced from CARS2 in the cells was determined by subtracting the amount of each sulfide in CARS2 KO HEK293T cells from that in the WT cells, after quantification of each metabolite via HPE-IAM labeling LC-MS/MS analysis. Changes in the amounts of CysSSH (ACysSSH) and HS— (AHS-) induced by complex III inhibition by antimycin A or by mtDNA elimination in WT and CARS2 KO HEK293T cells were then calculated.

Statistical analysis. Results are presented as means ±s.d. of at least three independent experiments unless otherwise specified. For statistical comparisons, we utilized two-tailed Student's t test or two-way analysis of variance followed by the Student-Newman-Keuls test, with significance set at $P<0.05$.

REFERENCES

The disclosures of the following papers, listed below, are incorporated herein by reference.
1. Toohey, J. I. Sulfur signaling: is the agent sulfide or sulfane? Anal. Biochem. 413, 1-7 (2011).
2. Fukuto, J. M. et al. Small molecule signaling agents: the integrated chemistry and biochemistry of nitrogen oxides, oxides of carbon, dioxygen, hydrogen sulfide, and their derived species. Chem. Res. Toxicol. 25, 769-793 (2012).
3. Ida, T. et al. Reactive cysteine persulfides and S-polythiolation regulate oxidative stress and redox signaling. Proc. Natl Acad. Sci. USA 111, 7606-7611 (2014).
4. Dóka, É. et al. A novel persulfide detection method reveals protein persulfide- and polysulfide-reducing functions of thioredoxin and glutathione systems. Sci. Adv. 2, e1500968 (2016).
5. Kunikata, H. et al. Metabolomic profiling of reactive persulfides and polysulfides in the aqueous and vitreous humors. Sci. Rep. 7, 41984 (2017).
6. Numakura, T. et al. Production of reactive persulfide species in chronic obstructive pulmonary disease. Thorax doi:10.1136/thoraxjnl-2016-209359 (2017).
7. Ono, K. et al. Redox chemistry and chemical biology of H2S, hydropersulfides, and derived species: implications of their possible biological activity and utility. Free Radic. Biol. Med. 77, 82-94 (2014).
8. Saund, S. S. et al. The chemical biology of hydropersulfides (RSSH): chemical stability, reactivity and redox roles. Arch. Biochem. Biophys. 588, 15-24 (2015).

9. Millikin, R. et al. The chemical biology of protein hydropersulfides: studies of a possible protective function of biological hydropersulfide generation. Free Radic. Biol. Med. 97, 136-147 (2016).
10. Fujii, S. et al. Redox signaling regulated by an electrophilic cyclic nucleotide and reactive cysteine persulfides. Arch. Biochem. Biophys. 595, 140-146 (2016).
11. Cavallini, D., Federici, G. & Barboni, E. Interaction of proteins with sulfide. Eur. J. Biochem. 14, 169-174 (1970).
12. Massey, V. & Edmondson, D. On the mechanism of inactivation of xanthine oxidase by cyanide. J. Biol. Chem. 245, 6595-6598 (1970).
13. Branzoli, U. & Massey, V. Evidence for an active site persulfide residue in rabbit liver aldehyde oxidase. J. Biol. Chem. 249, 4346-4349 (1974).
14. Takahashi, N. et al. Reactive sulfur species regulate tRNA methylthiolation and contribute to insulin secretion. Nucleic Acids Res. 45, 435-445 (2016).
15. Jung, M. et al. Protein polysulfidation-dependent persulfide dioxygenase activity of ethylmalonic encephalopathy protein 1. Biochem. Biophys. Res. Commun. 480, 180-186 (2016).
16. Wróbel, M. Sulfurtransferase activity and sulfur compound content in Rana temporaria brain following hibernation. Acta Neurobiol. Exp. 61, 69-72 (2001).
17. Cortese-Krott, M. M. et al. Key bioactive reaction products of the NO/H2S interaction are S/N-hybrid species, polysulfides, and nitroxyl. Proc. Natl Acad. Sci. USA 112, E4651-E4660 (2015).
18. Yamanishi, T. & Tuboi, S. The mechanism of the L-cystine cleavage reaction catalyzed by rat liver γ-cystathionase. J. Biochem. 89, 1913-1921 (1981).
19. Chen, W. et al. The development of fluorescent probes for visualizing intracellular hydrogen polysulfides. Angew. Chem. Int. Ed. Engl. 54, 13961-13965 (2015).
20. Nishida, M. et al. Hydrogen sulfide anion regulates redox signaling via electrophile sulfhydration. Nat. Chem. Biol. 8, 714-724 (2012).
21. Yadav, P. K. et al. Biosynthesis and reactivity of cysteine persulfides in signaling. J. Am. Chem. Soc. 138, 289-299 (2016).
22. Morikawa, T. et al. Hypoxic regulation of the cerebral microcirculation is mediated by a carbon monoxide-sensitive hydrogen sulfide pathway. Proc. Natl Acad. Sci. USA 109, 1293-1298 (2012).
23. Shirozu, K. et al. Cystathionine γ-lyase deficiency protects mice from galactosamine/lipopolysaccharide-induced acute liver failure. Antioxid. Redox. Signal. 20, 204-216 (2014).
24. Nakano, S. et al. Hyperhomocysteinemia abrogates fasting-induced cardioprotection against ischemia/reperfusion by limiting bioavailability of hydrogen sulfide anions. J. Mol. Med. 93, 879-889 (2015).
25. Fletcher, J. C. & Robson, A. The occurrence of bis-(2-amino-2-carboxyethyl) trisulfide in hydrolysates of wool and other proteins. Biochem. J. 87, 553-559 (1963).
26. Parker, A. J. & Kharasch, N. The scission of the sulfur-sulfur bond. Chem. Rev. 59, 583-628 (1959).
27. Abdolrasulnia, R. & Wood, J. L. Persulfide properties of thiocystine and related trisulfides. Bioorg. Chem. 9, 253-260 (1980).
28. Kice, J. L. Electrophilic and nucleophilic catalysis of the scission of the sulfur-sulfur bond. Acc. Chem. Res. 1, 58-64 (1968).
29. Aviner, R., Geiger, T. & Elroy-Stein, O. Genome-wide identification and quantification of protein synthesis in cultured cells and whole tissues by puromycin-associated nascent chain proteomics (PUNCH-P). Nat. Protoc. 9, 751-760 (2014).
30. Hallmann, K. et al. A homozygous splice-site mutation in CARS2 is associated with progressive myoclonic epilepsy. Neurology 83, 2183-2187 (2014).
31. Coughlin, C. R. II. et al. Mutations in the mitochondrial cysteinyl-tRNA synthase gene, CARS2, lead to a severe epileptic encephalopathy and complex movement disorder. J. Med. Genet. 52, 532-540 (2015).
32. Eidenschenk C. et al. Record for madcow. Updated 13th May 2016. Center for the Genetics of Host Defense, UT Southwestern, Dallas, TX, USA Available at https://mutagenetix.utsouthwestern.edu/phenotypic/phenotypic_rec.cfm? pk=316. (Accessed 30th January 2017)
33. Akhtar, M. W. et al. Elevated glucose and oligomeric O-amyloid disrupt synapses via a common pathway of aberrant protein S-nitrosylation. Nat. Commun. 7, 10242 (2016).
34. Griesbeck, C. et al. Mechanism of sulfide-quinone reductase investigated using site-directed mutagenesis and sulfur analysis. Biochemistry 41, 11552-11565 (2002).
35. Grieshaber, M. K. & Volkel, S. Animal adaptations for tolerance and exploitation of poisonous sulfide. Annu. Rev. Physiol. 60, 33-53 (1998).
36. Goubern, M., Andriamihaja, M., Nibel, T., Blachier, F. & Bouillaud, F. Sulfide, the first inorganic substrate for human cells. FASEB J. 21, 1699-1706 (2007).
37. Hine, C. et al. Endogenous hydrogen sulfide production is essential for dietary restriction benefits. Cell 160, 132-144 (2015).
38. Szabo, C. et al. Regulation of mitochondrial bioenergetic function by hydrogen sulfide. Part I. Biochemical and physiological mechanisms. Br. J. Pharmacol. 171, 2099-2122 (2014).
39. Stehling, O. & Lill, R. The role of mitochondria in cellular iron-sulfur protein biogenesis: mechanisms, connected processes, and diseases. Cold Spring Harb. Perspect. Biol. 5, a011312 (2013).
40. Sawa, T. et al. Protein S-guanylation by the biological signal 8-nitroguanosine 3',5'-cyclic monophosphate. Nat. Chem. Biol. 3, 727-735 (2007).
41. Abiko, Y. et al. Involvement of reactive persulfides in biological bismethylmercury sulfide formation. Chem. Res. Toxicol. 28, 1301-1306 (2015).
42. Nishida, M. et al. Redox regulation of electrophilic signaling by reactive persulfides in cardiac cells. Free Radic. Biol. Med. 109, 132-140 (2017).
43. Wakasugi, K. & Schimmel, P. Two distinct cytokines released from a human aminoacyl-tRNA synthetase. Science 284, 147-151 (1999).
44. Suzuki, T., Ueda, T. & Watanabe, K. A new method for identifying the amino acid attached to a particular RNA in the cell. FEBS Lett. 381, 195-198 (1996).
45. Nissen, P., Hansen, J., Ban, N. P. B. & Steitz, A. The structural basis of ribosome activity in peptide bond synthesis. Science 289, 920-930 (2000).
46. Voss, N. R., Gerstein, M., Steitz, T. A. & Moore, P. B. The geometry of the ribosomal polypeptide exit tunnel. J. Mol. Biol. 360, 893-906 (2006).
47. Kramer, G., Boehringer, D., Ban, N. & Bukau, B. The ribosome as a platform for co-translational processing, folding and targeting of newly synthesized proteins. Nat. Struct. Mol. Biol. 16, 589-597 (2009).

48. Naito, Y., Hino, K., Bono, H. & Ui-Tei, K. CRISPRdirect: software for designing CRISPR/Cas guide RNA with reduced off-target sites. Bioinformatics 31, 1120-1123 (2015).
49. Ran, F. A. et al. Double nicking by RNA-guided CRISPR Cas9 for enhanced genome editing specificity. Cell 154, 1380-1389 (2013).
50. Mashiko, D. et al. Generation of mutant mice by pronuclear injection of circular plasmid expressing Cas9 and single guided RNA. Sci. Rep. 3, 3355 (2013).
51. Kaplon, J. et al. A key role for mitochondrial gatekeeper pyruvate dehydrogenase in oncogene-induced senescence. Nature 498, 109-112 (2013).
52. King, M. P. & Attardi, G. Isolation of human cell lines lacking mitochondrial DNA. Methods Enzymol. 264, 304-313 (1996).

Memorandum of the Drawings

In FIG. 1, formation of cysteine persulfide (CysSSH) and CysS-(S)n-H in proteins and their biosynthesis by EcCARS. a Quantitative identification by LC-MS/MS analysis of CysS-(S)n-H formed in recombinant ADH5 after pronase digestion of the HPE-IAM-labeled protein. b Formation of cysteine (CysSH) and CysS-(S)n-H on tRNA (Cys-tRNA-CysS-(S)n-H) as identified by HPE-IAM labeling LC-MS/MS analysis, which determined the amounts of CysSH and CysS—(S)n-H released from Cys-tRNACys and Cys-tRNA-CysS-(S)n-H synthesized in the EcCARS enzymatic reaction after their heat or alkaline treatment. The method employed is illustrated in the upper panel. c GAPDH cysteine polysulfides are formed and incorporated into nascent polypeptides synthesized de novo in ribosomes, as identified by PUNCH-PsP (FIGS. 10A and 10B; cf. Supplementary FIG. 6). d CysS-(S)n-H formation from cysteine, catalyzed by EcCARS, as dependent on enzyme and substrate (cysteine) concentrations and reaction time (lower panel). Schematic representation of the EcCARS-catalyzed reaction (upper panel). HPE-AM, β-(4-hydroxyphenyl)ethyl acetamide; HPE-IAM, 0-(4-hydroxyphenyl)ethyl iodoacetamide. Data a, b are means ±s.d. (n=3).

Figure 2:
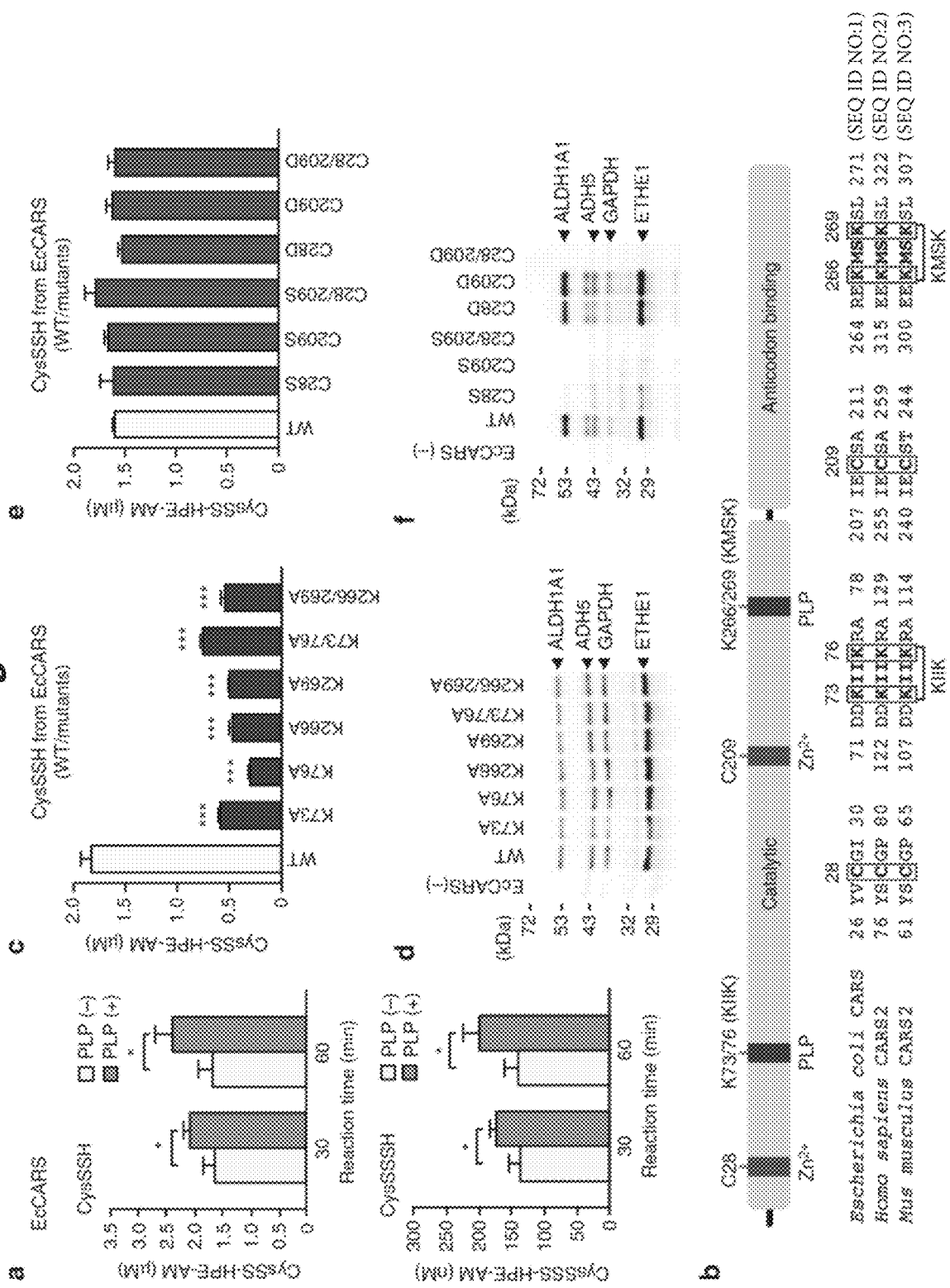
FIG. 2 shows CysS-(S)n-H biosynthesis.

In FIG. 2, CysS-(S)n-H biosynthesis catalyzed by EcCARS and its various mutant EcCARSs. a CysS-(S)n-H (CysSSH and CysSSSH) biosynthesis from cysteine catalyzed by EcCARS as a function of reaction time and the presence or absence of PLP. CysS-(S)n-H production was analyzed by using the HPE-IAM labeling with LC-MS/MS analysis for the reaction of recombinant EcCARS (200 μg/ml) with 100 μM cysteine in the presence or absence of 50 μM PLP. The data are means ±s.d. (n=3). *P<0.05. b General structure (upper panel) and conserved amino acid alignments (lower panel) of bacterial, human, and rodent CARSs. c, e Enzyme activities of EcCARS lysine (K) mutants c and cysteine (C) mutants e to form CysSSH. WT and EcCARS K and C mutants, 200 μg/ml each, reacted with 25 μM cysteine at 37° C. for 30 min. Data represent means ±s.d. (n=3). ***P<0.001. The enzyme activity of EcCARS Lys (d) and Cys (f) mutants was assessed by the PUREfrex assay with the cell-free translational reactions for ALDH1A1 (55 kDa), ADH5 (40 kDa), GAPDH (36 kDa), and ETHEl (28 kDa), with protein syntheses being identified by western blotting.

Figure 3:
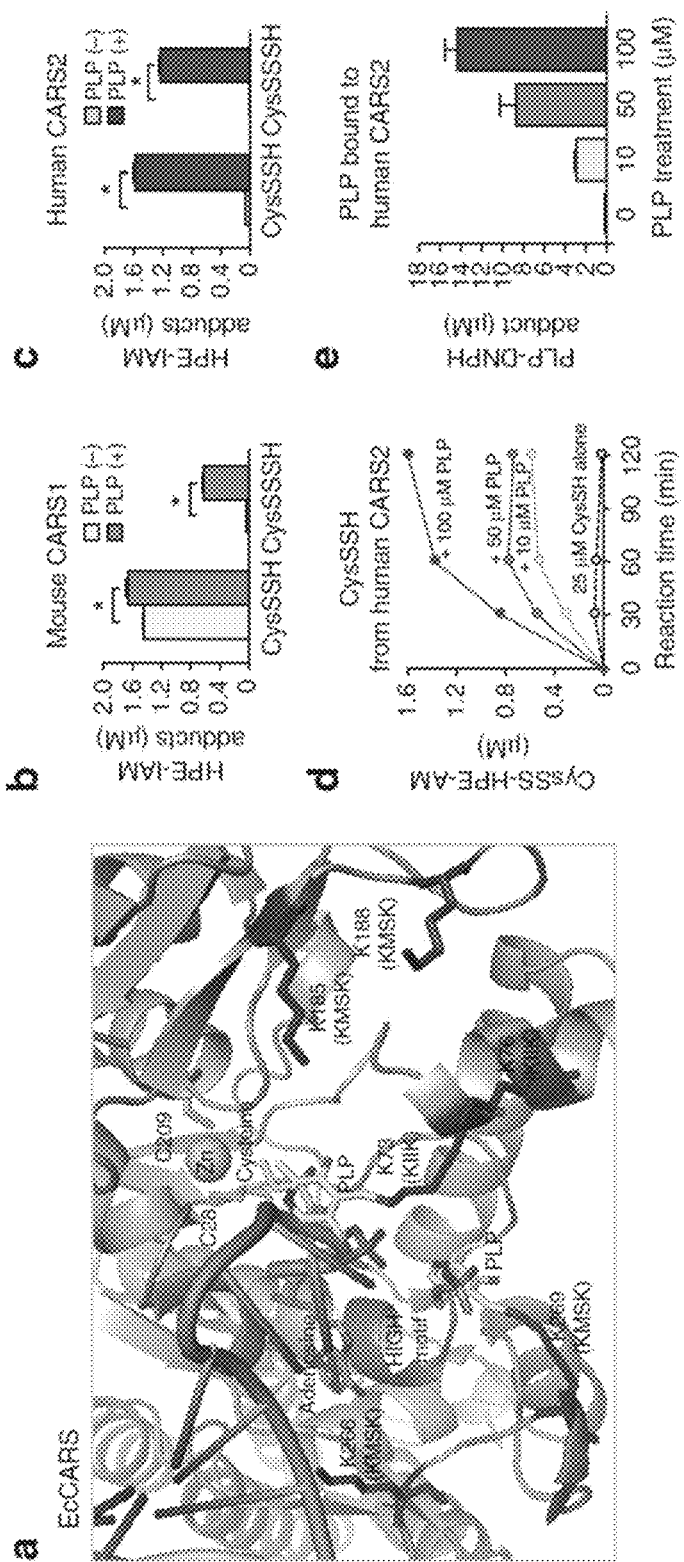
FIG. 3 shows computational modeling of EcCARS structure.

In FIG. 3, computational modeling of EcCARS structure, and CysS-(S)n-H biosynthesis by CARS1/2. a molecular docking model of PLP-bound EcCARS generated by SwissDock using the crystal structure of EcCARS (PDB ID: 1LI5). Cysteinyl-tRNA is placed by superimposing the crystal structure of the EcCARS-Cysteinyl-tRNA binary complex (PDB ID: 1U0B) to the docking model. b, c PLP-dependent CysSSH and CysSSSH biosynthesis by mouse CARS1 and human CARS2. CysSSH and CysSSSH production was quantified by means of HPE-IAM labeling LC-MS/MS analysis in the reaction of recombinant mouse CARS1 and human CARS2 (200 μg/ml each) with 25 μM L-cysteine in the presence or absence of 100 μM PLP (37° C., 2 h). The data are means ±s.d. (n=3). *P<0.01. d Concentration-dependent effects of PLP on CysSSH and CysSSSH production by recombinant human CARS2. Human CARS2 (200 μg/ml) reacted with 25 μM cysteine in the presence of 0, 10, 50, or 100 μM PLP at 37° C. for 30-120 min. No appreciable cysteine persulfide production was detected in the reaction mixture of cysteine and PLP alone as long as no>100 μM PLP was used. e Precisely quantitative analysis for PLP bound to human CRAS2. Human CARS2 treated with various concentrations of PLP (d) at 37° C. for 1 h was reacted with DNPH to form PLP-DNPH adduct, followed by quantification by LC-ESI-MS/MS analysis.

Figure 4:
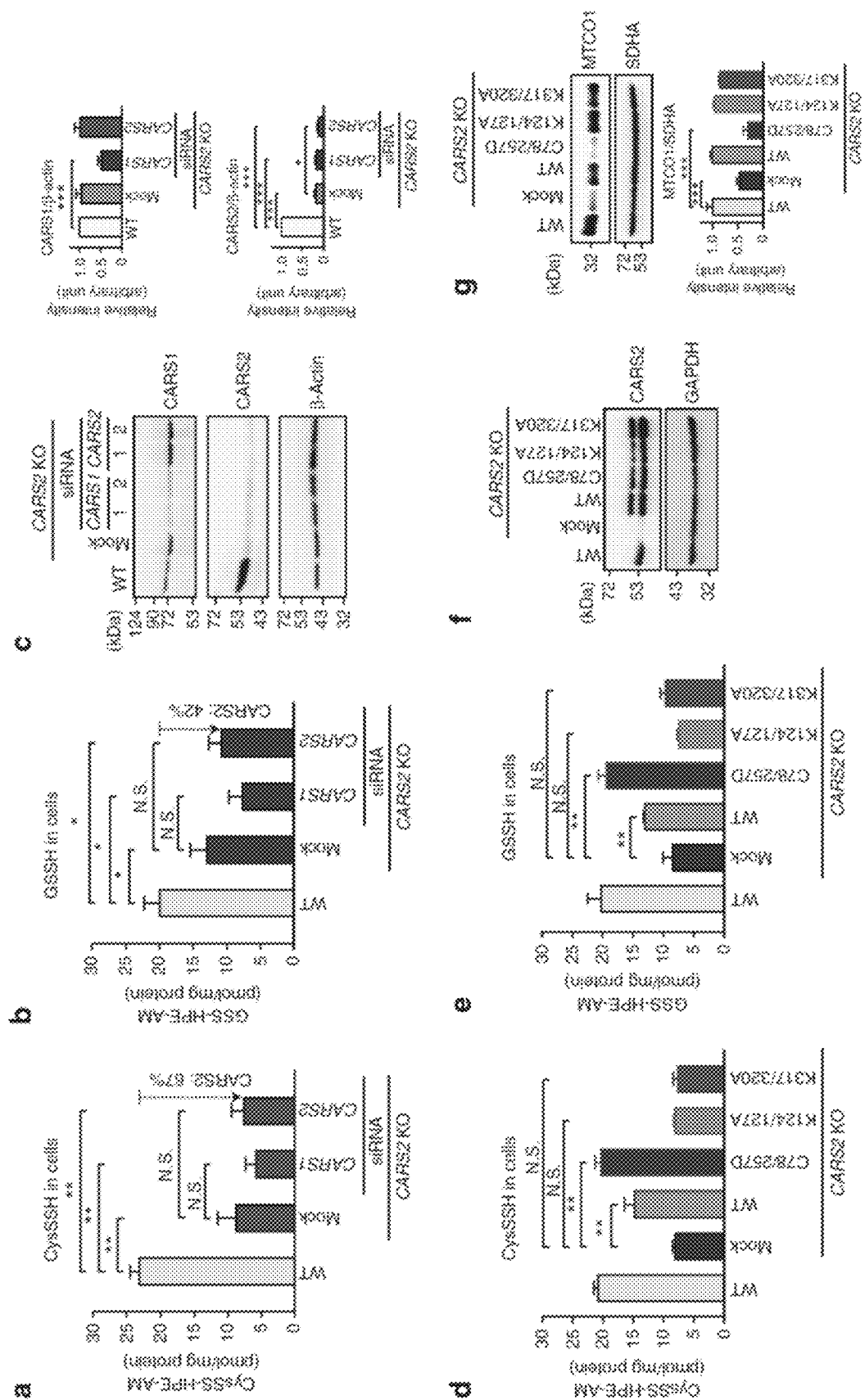
FIG. 4 shows endogenous formation of persulfides in HEK293T cells.

In FIG. 4, endogenous formation of persulfides in HEK293T cells. Intracellular levels of CysSSH (a) and GSSH (b) in WT and CARS2 KO cells with CARS1 or CARS2 knocked down. Data are means ±s.d. (n=3). *P<0.05; P<0.01; N.S., not significant. c CARS1 and CARS2 Western blotting for cells used in a and b. Lane 1 and 2, duplicate determinations with each siRNA. The right panel shows the densitometric analysis for the western blot shown in the right panel. The data are means ±s.d. (n=3). *P<0.001. Production of CysSSH (d) and GSSH (e) in CARS2 KO cells with WT or CARS2 C and K mutants added back. The data are means ±s.d. (n=3). P<0.01; N.S., not significant vs. CARS2 KO mock. f CARS2 western blotting for WT and CARS2 KO cells with WT or CARS2 C and K mutants added back. g Western blotting for the cells in d and e with different mitochondrial proteins: MTCO1, mitochondrial cytochrome c oxidase subunit 1 (encoded by mitochondrial DNA) and SDHA, succinate dehydrogenase complex flavoprotein subunit A (encoded by genomic DNA). The lower panel shows the densitometric analysis for the western blot. The data are means ±s.d. (n=3). *P<0.001. About the feature, the paper "RUDYK Et al, Oxidation of PKGIα mediates an endogenous adaptation to pulmonary hypertension, PNAS, 116 (26), page 13016-13025, June 2019" is incorporated by reference.

In FIG. 5, generation of Cars2-deficient mice via the CRISPR/CAS9 system. a Schematic illustration of the mouse Cars2 gene structure and sequences of WT and mutant alleles around the target locus. Green and black letters indicate the first exon and intron of Cars2, respectively. The targeted locus of gRNA and protospacer-adjacent motif (PAM) sequence were indicated in the WT sequence are indicated by underlined and bold letters, respectively. A modified allele sequence obtained from the Cars2-edited mouse (line 1) is shown below. b Detection of mutations introduced by gRNA-Cas9 targeting Cars2 via PCR with genomic DNA from WT and Cars2+/− mice. Cars2+/−, Cars2 heterozygous KO mice, M. DNA molecular weight marker. c Western blotting of CARS2 and mitochondrial proteins, e.g., MTCO1 and SDHA, from mitochondria isolated from the liver. The lower panel shows the densitometric analysis of the western blot. Data are means ±s.d. (n=3). ***P<0.001. d CysSSH production in mitochondria isolated from the liver of WT and Cars2+/− littermate mice. Various concentrations of isolated mitochondria were reacted with HPE-IAM for 1 h, followed by LC-MS/MS analysis (see Supplementary Methods for details). Mitochondria were obtained from line 2 Cars2+/− mice. *P<0.05, WT vs.

Cars2+/− mice (two-way ANOVA). e Western blotting of CARS1, CSE, CBS, and 3-MST with liver tissue obtained from WT and Cars2+/− mice. The right panels show the densitometric analysis of the CARS1 and CARS2 immunoblots. Data are means ±s.d. (n=3). ***P<0.001. About the features discussed in the paragraph, the papers, "M. IKEDA et al, Distribution of Polysulfide in Human Biological Fluids and Their Association with Amylase and Sperm Activities, Molecules, vol. 24,1689, 2019", "T. ZHANG et al, Enhanced Cellular Polysulfides Negatively Regulate TLR4 Signaling and Mitigate Lethal Endotoxin Shock, Cell Chemical Biology, 26, 686-698, May 16, 2019" and "T. TAKATA, The active-site cysteine residue of Ca2+/calmodulin-dependent protein kinase I is protected from irreversible modification via generation of polysulfidation, Nitric Oxide, 86, P68-75, 2019," are incorporated by reference.

In FIG. 6, in vivo formation of various sulfide species in WT and Cars2+/− mice. Endogenous production of CysSSH and other related polysulfide compounds was identified by means of HPE-IAM labeling LC-MS/MS analysis in the liver a and lung b obtained from WT and Cars2+/− littermates (21-week-old males). The data are means ±s.d. (n=3). *P<0.05; **P<0.01.

In FIG. 7, endogenous protein polysulfidation in vivo and in HEK293T cells. The amounts of CysSSH formed in whole cell protein recovered from the mouse livers of WT and Cars2+/−(line 1) 21-week-old male littermates (a) and from WT and CARS2 KO HEK293T cells (b) were quantified by using HPE-IAM labeling LC-MS/MS analysis. Data are means ±s.d. (n=3). *P<0.05; **P<0.01. c Schematic drawing of the mechanism of the extramitochondrial release of CysSSH into the cytosol, which may regulate whole cell protein polysulfidation.

Figure 8:
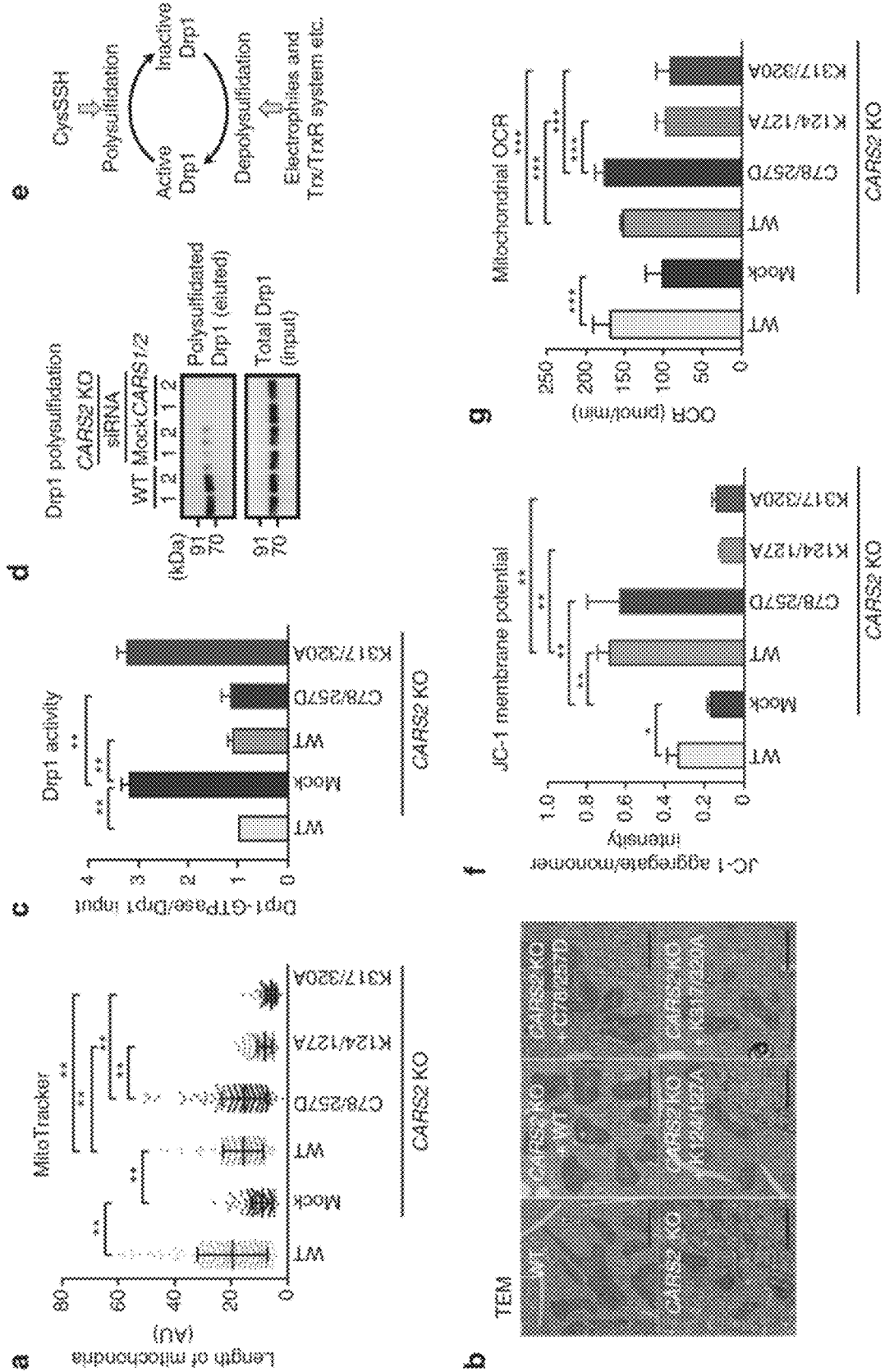
FIG. 8 shows CARS2-dependent mitochondrial morphogenesis and bioenergetics.

In FIG. 8, CARS2-dependent mitochondrial morphogenesis and bioenergetics. a Mitochondrial morphological analyses with MitoTracker Red fluorescent mitochondrial stain: morphometric analysis of mitochondrial length in HEK293T cells (WT and CARS2 KO; CARS2 WT and mutants added back). AU, arbitrary unit. The data are means ±s.d. (n=3). P<0.01. b Transmission electron microscope (TEM) images of the cells in a. Scale bars, 1 μm. c Identification of Drp1 activity in HEK293T cells (WT and CARS2 KO; CARS2 WT and mutants added back). The GTP-agarose pulldown assay was performed. The data are means ±s.d. (n=3). P<0.01. d Drp1 expressed in extensively polysulfidated (biotin-PEG-MAL capture method) HEK293T cells. Drp1 was markedly suppressed and nullified by CARS2 KO and CARS1/2 knockdown. Lanes 1 and 2 show duplicate determinations with each siRNA. About the full blot images discussed here, a paper, "J. LIN et al, The Uptake and Release of Polysulfur Cysteine Species by Cells: Physiological and Toxicological Implications, Chemical Research in Toxicology, 32, p 447-455, 2019," is incorporated by reference. A schematic drawing of Drp1 activity as regulated by protein polysulfidation and depolysulfidation, as affected by polysulfides vs. electrophiles and Trx/TrxR system. f Changes in membrane potential as assessed by using JC-1 staining of HEK293T cells (WT and CARS2 KO; CARS2 WT and mutants added back). The data are means ±s.d. (n=3). *P<0.05; P<0.01. g Assessment of mitochondrial electron flow in HEK293T CARS2 KO cells with or without adding back WT and C78/257D, K124/127A, and K317/320A mutants, as analyzed by measuring OCR using an extracellular flux analyzer. Time dependence of oxygen consumption before/after inhibition of mitochondrial respiration at complexes I and III by rotenone/antimycin A, and its statistical summary; the data are means s.d. (n=3). *P<0.001.

In FIG. 9, mitochondrial ETC-mediated reduction of CysSSH. a, b Sulfide metabolite profiling for the reaction of the recombinant human CARS2 in vitro (a) and of CARS2 expressed in HEK293T cells (b). c-h Changes in amounts of CysSSH (ΔCysSSH) and HS— (AHS-) induced by complex III inhibition by antimycin A c-e or by mitochondrial DNA (mtDNA) elimination induced by ethidium bromide (f-h) in WT and CARS2 KO HEK 293 T cells. The values of CysSSH and HS— shown in b-h indicate the quantity of each compound produced in the cells in a manner dependent on CARS2 expression, which was determined by subtracting each amount in CARS2 KO HEK293T cells from that in the WT cells, after quantification of each metabolite via HPE-IAM labeling LC-MS/MS analysis. e, h Stoichiometric alterations (conversion) between CysSSH and HS— in cells by the ETC inhibition. i Schematic diagram of ETC-mediated CysSSH reduction to form HS— and possible further conversion to S2O32-. The data are means ±s.d. (n=3). *P<0.05; **P<0.01; N.S., not significant.

In FIGS. 10A and 10B, CARS-mediated protein polysulfidation and mitochondrial functions. a The physiological relevance of co-translational protein polysulfidation that is reversibly regulated by various post-translational modifications, including depolysulfidation. b A CysS-(S)n-H regulation mechanism for mitochondrial functions with regard to mitochondrial biogenesis and bioenergetics. CysSSH is reductively metabolized to CysSH and HS—, which may be oxidized by sulfide:quinone reductase (SQR) and other enzymes, e.g., sulfur dioxygenase (SD) and sulfur transferase (ST), in a manner linked to ETC in mitochondria. The CysS-(S)n-H-dependent HS— metabolism may be coupled with formation of the iron-sulfur clusters, as being controlled by the mitochondrial ETC. I, II, III, and IV: complexes I, II, III, and IV; TCA tricarboxylic acid (Krebs) cycle.

[Explanations with Respect to FIGS. 11A-11D]

Figure 11A:
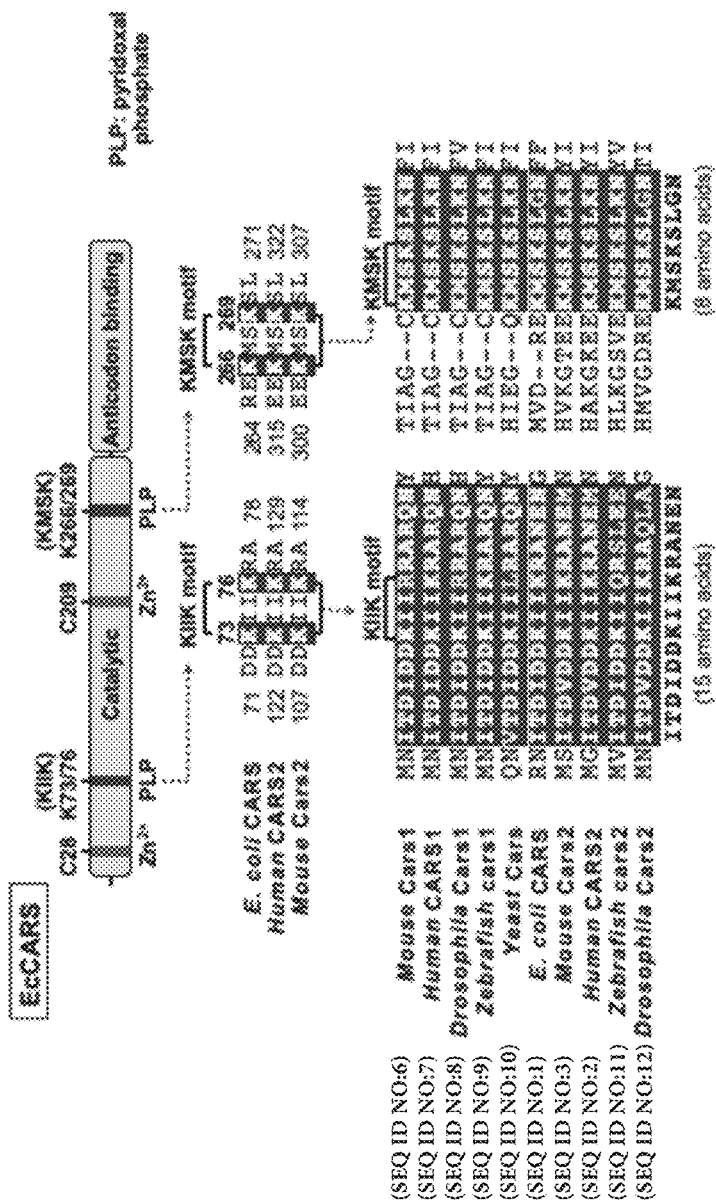
FIGS. 11A-11D show data related to the invention.
Figure 11C:
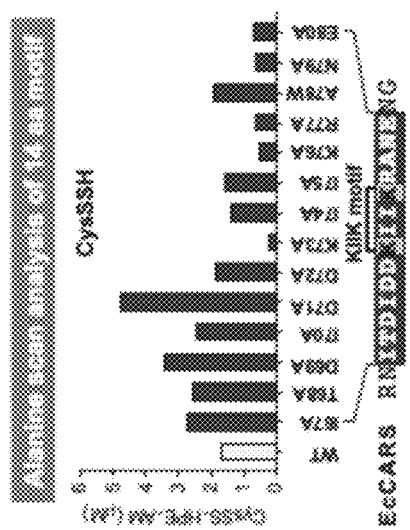
Figure 11B:
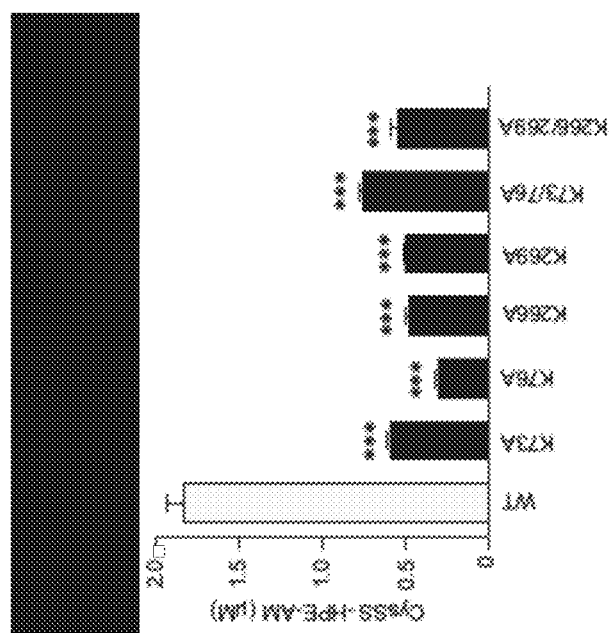
Figure 11D:
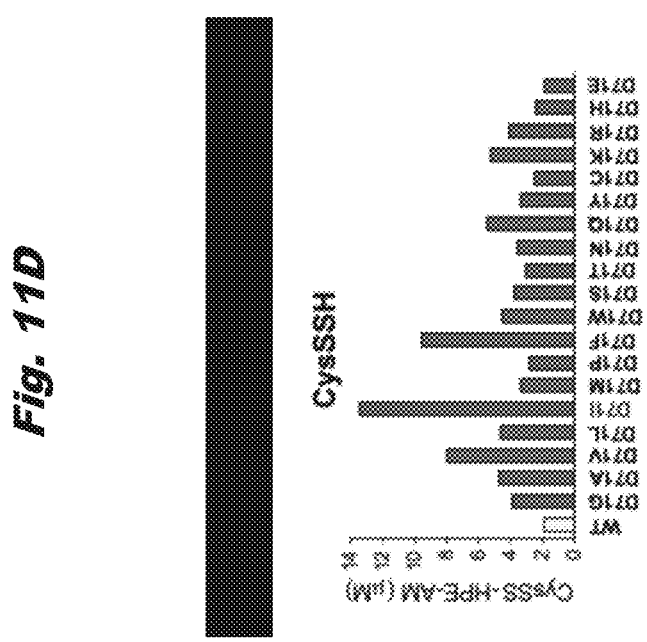

FIG. 11A As shown here by the primary structure of *Escherichia coli* CARS (EcCARS) and sequence alignments of amino acids around KIIK and KMSK motifs of EcCARS, we found that the amino acid sequences surrounding KIIK/KMSK motifs of EcCARS, i.e., 15 amino acids and 8 amino acids for KIIK and KMSK, respectively, are completely conserved among all species. This interpretation is not published yet.

FIG. 11B

Cysteine persulfide synthesis (CPERS) activity of recombinant EcCARS mutants of lysine 73, 76, 266 and 269 residues, which are CPERS catalytic sites because of PLP-binding (so, we just called simply as PLP-binding sites), and were substituted with alanine, was quantitatively measured by using LC-MS/MS analysis. CPERS activities of these lysine mutants of EcCARS were remarkably decreased, compared with wild-type (WT). This revealed that KIIK and KIMSK are active center of CPERS, indeed. This data are already reported in Akaike et al. Nat Commun 2017.

FIG. 11C

CPERS activities of recombinant EcCARS, in which amino acids around the KIIK motif highly conserved were substituted with alanine, were quantitatively measured by using LCMS/MS analysis (so called alanine scan technique). EcCARS K73A and K76A mutants (KIIK motif lysine 73/76 substituted with alanine) showed significantly low CPERS activities. On the other hand, EcCARS D71A mutant (aspartate 71 upstream of the KIIK motif substituted with alanine), showed a significantly high CPERS activity, compared with the wild type (WT). This indicates that the 15 amino acid KIIK-surrounding motif has a regulatory function to control the overproduction of persulfides from CARS. In other words, this is a discovery of the new function of the KIIK surrounding 15 amino acid motif of CARS. This is not published yet.

FIG. 11D

Since alanine scan analysis showed higher CPERS activity of EcCARS D71A, the CPERS activity of mutants for aspartate 71 substituted with other 19 amino acids were quantitatively analyzed using LC-MS/MS. As a result, EcCARS D71I (aspartate 71 substituted to isoleucine, a highly hydrophobic amino acid), showed the highest CPERS activity.

This indicates that the mutation of aspartate, a hydrophilic amino acid, to the hydrophobic amino acid, may cause the structural change of the KIIK motif, thereby leading to the enhanced PLP-binding capacity and finally increased CPERS activity. This data is not published yet.

What is claimed:

1. A method of synthesizing cysteine hydropersulfide (CysSSH) in vitro, comprising:
   providing a L-cysteine substrate;
   performing a reaction catalyzed by cysteinyl-tRNA synthetases (CARSs) in HEPES buffer in the absence of ATP and tRNA to synthesize said cysteine hydropersulfide (CysSSH).

2. The method of synthesizing cysteine hydropersulfide (CysSSH) according to claim 1, wherein the pH of the HEPIES buffer is 7.5.

3. The method of synthesizing cysteine hydropersulfide (CysSSH) according to claim 1, wherein the HEPES buffer contains KCl and MgCl2.

4. The method of synthesizing cysteine hydropersulfide (CysSSH) according to claim 3, wherein the reaction catalyzed by the CARSs is performed at 37° C. for 15-60 min.

* * * * *